United States Patent
Henkin et al.

(10) Patent No.: US 10,583,199 B2
(45) Date of Patent: Mar. 10, 2020

(54) NANOCARRIERS HAVING SURFACE CONJUGATED PEPTIDES AND USES THEREOF FOR SUSTAINED LOCAL RELEASE OF DRUGS

(71) Applicant: Northwestern University, Evanston, IL (US)

(72) Inventors: Jack Henkin, Highland Park, IL (US); Ignacio Melgar-Asensio, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/807,034

(22) Filed: Nov. 8, 2017

(65) Prior Publication Data

US 2018/0092988 A1 Apr. 5, 2018

Related U.S. Application Data

(63) Continuation-in-part of application No. 15/497,822, filed on Apr. 26, 2017, now Pat. No. 10,081,668.

(60) Provisional application No. 62/420,344, filed on Nov. 10, 2016, provisional application No. 62/327,767, filed on Apr. 26, 2016.

(51) Int. Cl.
| | |
|---|---|
| *A61K 47/69* | (2017.01) |
| *C07K 7/06* | (2006.01) |
| *A61K 9/00* | (2006.01) |
| *C07K 14/81* | (2006.01) |
| *C07K 14/78* | (2006.01) |
| *C07K 14/75* | (2006.01) |
| *C07K 14/47* | (2006.01) |
| *A61K 47/61* | (2017.01) |
| *A61K 47/54* | (2017.01) |
| *A61K 38/00* | (2006.01) |

(52) U.S. Cl.
CPC ........ *A61K 47/6939* (2017.08); *A61K 9/0048* (2013.01); *A61K 9/0051* (2013.01); *A61K 47/542* (2017.08); *A61K 47/61* (2017.08); *A61K 47/6903* (2017.08); *A61K 47/6921* (2017.08); *A61K 47/6935* (2017.08); *C07K 7/06* (2013.01); *C07K 14/47* (2013.01); *C07K 14/75* (2013.01); *C07K 14/78* (2013.01); *C07K 14/811* (2013.01); *C07K 14/8121* (2013.01); *A61K 38/00* (2013.01)

(58) Field of Classification Search
CPC .............................. A61K 47/6939; C07K 7/06
See application file for complete search history.

(56) References Cited

U.S. PATENT DOCUMENTS

| | | |
|---|---|---|
| 5,443,458 A | 8/1995 | Eury |
| 5,670,161 A | 9/1997 | Healy et al. |
| 5,766,710 A | 6/1998 | Turnland et al. |
| 5,788,979 A | 8/1998 | Alt et al. |
| 5,980,551 A | 11/1999 | Summers et al. |
| 6,527,801 B1 | 3/2003 | Dutta |
| 6,699,272 B2 | 3/2004 | Slepian et al. |
| 6,709,452 B1 | 3/2004 | Valimaa et al. |
| 6,830,747 B2 | 12/2004 | Lang et al. |
| 7,094,260 B2 | 8/2006 | Jing et al. |
| 7,128,755 B2 | 10/2006 | Su et al. |
| 7,390,333 B2 | 6/2008 | Dutta |
| 7,396,531 B2 * | 7/2008 | Rath ........................ C12N 7/00 424/185.1 |
| 7,396,664 B2 | 7/2008 | Daly et al. |
| 7,470,283 B2 | 12/2008 | Dutta |
| 2002/0019661 A1 | 2/2002 | Datta et al. |
| 2002/0082610 A1 | 6/2002 | Cioanta et al. |
| 2002/0143388 A1 | 10/2002 | Datta et al. |
| 2002/0183830 A1 | 12/2002 | Su et al. |
| 2003/0027940 A1 | 2/2003 | Lang et al. |
| 2003/0045924 A1 | 3/2003 | Datta et al. |
| 2003/0097173 A1 | 5/2003 | Dutta et al. |
| 2003/0105245 A1 | 6/2003 | Amsden et al. |
| 2003/0105518 A1 | 6/2003 | Dutta |
| 2003/0109647 A1 | 6/2003 | Lang et al. |
| 2003/0118692 A1 | 6/2003 | Wang et al. |
| 2003/0144730 A1 | 7/2003 | Datta et al. |
| 2003/0153971 A1 | 8/2003 | Chandrasekaran |
| 2003/0153972 A1 | 8/2003 | Helmus |
| 2004/0230316 A1 | 11/2004 | Cioanta et al. |
| 2004/0260386 A1 | 12/2004 | Shalaby |
| 2005/0010280 A1 | 1/2005 | Jing et al. |
| 2005/0019404 A1 | 1/2005 | Sung et al. |
| 2005/0169968 A1 | 8/2005 | Elmaleh et al. |
| 2005/0177246 A1 | 8/2005 | Datta et al. |
| 2005/0232971 A1 | 10/2005 | Hossainy et al. |

(Continued)

FOREIGN PATENT DOCUMENTS

WO WO 2012/138731 10/2012

OTHER PUBLICATIONS

Altschul et al., Basic local alignment search tool. J Mol Biol. Oct. 5, 1990;215(3):403-10.
Araujo et al., Release profile and transscleral permeation of triamcinolone acetonide loaded nanostructured lipid carriers (TA-NLC): in vitro and ex vivo studies. Nanomedicine. Aug. 2012;8(6):1034-41.
Jin et al., Anti-inflammatory and antiangiogenic effects of nanoparticle-mediated delivery of a natural angiogenic inhibitor. Invest Ophthalmol Vis Sci. Aug. 5, 2011;52(9):6230-7.
Kim et al., Investigating the movement of intravitreal human serum albumin nanoparticles in the vitreous and retina. Pharm Res. Feb. 2009;26(2):329-37.

(Continued)

*Primary Examiner* — Amber D Steele
(74) *Attorney, Agent, or Firm* — Casimir Jones SC; David W. Staple

(57) ABSTRACT

Disclosed are biodegradable nanocarriers that have a net positive surface charge and zeta potential between about +2 to about +20 mV. The positive surface charge of the nanocarriers is provided by peptides that are covalently attached to the surface of the nanocarriers. The nanocarriers may comprise a drug and may be administered for localized and sustained delivery of the drug.

19 Claims, 14 Drawing Sheets

Specification includes a Sequence Listing.

(56) References Cited

U.S. PATENT DOCUMENTS

| | | |
|---|---|---|
| 2005/0267565 A1 | 12/2005 | Dave et al. |
| 2005/0278015 A1 | 12/2005 | Dave et al. |
| 2005/0283224 A1 | 12/2005 | King et al. |
| 2006/0002979 A1 | 1/2006 | Ashammakhi et al. |
| 2006/0009839 A1 | 1/2006 | Tan et al. |
| 2006/0018948 A1 | 1/2006 | Guire et al. |
| 2006/0051394 A1 | 3/2006 | Moore et al. |
| 2006/0147491 A1 | 7/2006 | DeWitt et al. |
| 2006/0193892 A1 | 8/2006 | Furst et al. |
| 2006/0198868 A1 | 9/2006 | DeWitt et al. |
| 2006/0264531 A1 | 11/2006 | Zhao et al. |
| 2006/0286138 A1 | 12/2006 | Malshe et al. |
| 2006/0287710 A1 | 12/2006 | Lendlein et al. |
| 2007/0005130 A1 | 1/2007 | Glauser et al. |
| 2007/0014831 A1 | 1/2007 | Sung et al. |
| 2007/0043433 A1 | 2/2007 | Chandrasekaran |
| 2007/0043434 A1 | 2/2007 | Meerkin et al. |
| 2007/0050018 A1 | 3/2007 | Wainwright |
| 2007/0106371 A1 | 5/2007 | Datta et al. |
| 2007/0123973 A1 | 5/2007 | Roth et al. |
| 2007/0129790 A1 | 6/2007 | Peng |
| 2007/0129793 A1 | 6/2007 | Su et al. |
| 2007/0141100 A1 | 6/2007 | Sung et al. |
| 2007/0196423 A1 | 8/2007 | Ruane et al. |
| 2007/0203564 A1 | 8/2007 | Rusk et al. |
| 2007/0219626 A1 | 9/2007 | Rolando et al. |
| 2007/0224234 A1 | 9/2007 | Steckel et al. |
| 2007/0224244 A1 | 9/2007 | Weber et al. |
| 2007/0224247 A1 | 9/2007 | Chudzik et al. |
| 2007/0237803 A1 | 10/2007 | Cheng et al. |
| 2007/0264307 A1 | 11/2007 | Chen et al. |
| 2007/0275033 A9 | 11/2007 | Moore et al. |
| 2007/0281117 A1 | 12/2007 | Kaplan et al. |
| 2007/0287987 A1 | 12/2007 | Katsearava et al. |
| 2007/0288088 A1 | 12/2007 | Bureau et al. |
| 2007/0298066 A1 | 12/2007 | Alferiev et al. |
| 2008/0008735 A1 | 1/2008 | Diener |
| 2008/0103583 A1 | 1/2008 | Imai et al. |
| 2008/0051880 A1 | 2/2008 | Gale et al. |
| 2008/0069858 A1 | 3/2008 | Weber |
| 2008/0071357 A1 | 3/2008 | Girton et al. |
| 2008/0091262 A1 | 4/2008 | Gale et al. |
| 2008/0119927 A1 | 5/2008 | Lessar |
| 2008/0152690 A1 | 6/2008 | Kohn et al. |
| 2008/0154351 A1 | 6/2008 | Leewood et al. |
| 2008/0220048 A1 | 9/2008 | Chen et al. |
| 2008/0233168 A1 | 9/2008 | Cheng et al. |
| 2008/0233169 A1 | 9/2008 | Chen et al. |
| 2008/0243240 A1 | 10/2008 | Doty et al. |
| 2008/0249633 A1 | 10/2008 | Wu |
| 2009/0004243 A1 | 1/2009 | Pacetti et al. |
| 2009/0105352 A1 | 1/2009 | Bezwada |
| 2009/0081270 A9 | 3/2009 | Moore et al. |
| 2009/0082853 A1 | 3/2009 | Dutta |
| 2009/0110713 A1 | 4/2009 | Lim et al. |
| 2009/0117039 A1 | 5/2009 | Richard |
| 2009/0149568 A1 | 6/2009 | Pacetti |
| 2009/0171455 A1 | 7/2009 | Benco et al. |
| 2009/0182404 A1 | 7/2009 | Shokoohi |
| 2009/0182415 A1 | 7/2009 | Wang |
| 2009/0192588 A1 | 7/2009 | Shin et al. |
| 2009/0232863 A1 | 9/2009 | Cheng et al. |
| 2009/0299465 A1 | 12/2009 | Shalaby |
| 2010/0172943 A1* | 7/2010 | Edelson ............ A61K 8/044 424/401 |
| 2011/0262963 A1* | 10/2011 | Geierstanger ....... C07D 207/20 435/68.1 |
| 2013/0210724 A1* | 8/2013 | Fetzer ................ B82Y 5/00 514/7.8 |
| 2014/0193508 A1* | 7/2014 | Bajpayee ............ A61K 9/0019 424/499 |
| 2014/0234382 A1* | 8/2014 | Edelson ............ A61K 8/044 424/401 |
| 2015/0231274 A1* | 8/2015 | Cheng ................ C12N 15/87 530/322 |

OTHER PUBLICATIONS

Li et al., Sustaining Intravitreal Residence With L-Arginine Peptide-Conjugated Nanocarriers. Invest Ophthalmol Vis Sci. Oct. 1, 2017;58(12):5142-5150.

Liu et al., A lipid nanoparticle system improves siRNA efficacy in RPE cells and a laser-induced murine CNV model. Invest Ophthalmol Vis Sci. Jul. 1, 2011;52(7):4789-94.

Marano et al., Inhibition of in vitro VEGF expression and choroidal neovascularization by synthetic dendrimer peptide mediated delivery of a sense oligonucleotide. Exp Eye Res. Oct. 2004;79(4):525-35.

Marano et al., Dendrimer delivery of an anti-VEGF oligonucleotide into the eye: a long-term study into inhibition of laser-induced CNV, distribution, uptake and toxicity. Gene Ther. Nov. 2005;12(21):1544-50.

Park et al., Nanoparticle-mediated expression of an angiogenic inhibitor ameliorates ischemia-induced retinal neovascularization and diabetes-induced retinal vascular leakage. Diabetes. Aug. 2009;58(8):1902-13.

Pepic et al., A nonionic surfactant/chitosan micelle system in an innovative eye drop formulation. J Pharm Sci. Oct. 2010;99(10):4317-25.

Tatusova et al., BLAST 2 Sequences, a new tool for comparing protein and nucleotide sequences. FEMS Microbiol Lett. May 15, 1999;174(2):247-50.

Thakur et al., Strategies for ocular siRNA delivery: Potential and limitations of non-viral nanocarriers. J Biol Eng. Jun. 11, 2012;6(1):7.

Turchinovich et al., Non-viral siRNA delivery into the mouse retina in vivo. BMC Ophthalmol. Oct. 1, 2010;10:25.

International Search Report and Written Opinion for PCT/US2017/060596, dated Feb. 14, 2018, 8 pages.

S.K. Bhattacharya, Retinal Deimination in Aging and Disease, Iubmb Life, 61 (2009) 504-509.

A. Chaudhuri, P. E. Hallett, J.A. Parker, Aspheric curvatures, refractive indices and chromatic aberration for the rat eye, Vision Res, 23 (1983) 1351-1363.

J. Crank, The mathematics of diffusion, Oxford university press, 1979.

K.G. Falavarjani, Q.D. Nguyen, Adverse events and complications associated with intravitreal injection of anti-VEGF agents: a review of literature, Eye, 27 (2013) 787-794.

H. Kim, S.B. Robinson, K.G. Csaky, Investigating the movement of intravitreal human serum albumin nanoparticles in the vitreous and retina, Pharmaceutical research, 26 (2009) 329-337.

H. Li, W. Liu, H.F. Zhang, Investigating the influence of chromatic aberration and optical illumination bandwidth on fundus imaging in rats, J. Biomed. Opt., 20 (2015) 106010.

National Eye Institute, Prevalence of Adult Vision Impairment and Age-Related Eye Diseases in America, https://nei.nih.gov/eyedata/adultvision_usa, 2016.

T.H. Senanayake, G. Warren, S.V. Vinogradov, Novel Anticancer Polymeric Conjugates of Activated Nucleoside Analogues, Bioconjugate Chemistry, 22 (2011) 1983-1993.

K. S. Tsai, M. H. Grayson, Pulmonary defense mechanisms against pneumonia and sepsis. Curr Opin Pulm Med 14, 260-265 (2008).

I. Wasiak, A. Kulikowska, M. Janczewska, M. Michalak, I.A. Cymerman, A. Nagalski, P. Kallinger, W.W. Szymanski, T. Ciach, Dextran Nanoparticle Synthesis and Properties, Plos One, 11 (2016).

Q.G. Xu, N. J. Boylan, J.S. Suk, Y.Y. Wang, E.A. Nance, J.C. Yang, P.J. McDonnell, R.A. Cone, E.J. Duh, J. Hanes, Nanoparticle diffusion in, and microrheology of, the bovine vitreous ex vivo, Journal of Controlled Release, 167 (2013) 76-84.

(56) References Cited

OTHER PUBLICATIONS

B.J. Zern, H. Chu, A.O. Osunkoya, J. Gao, Y. Wang, A Biocompatible Arginine-Based Polycation, Advanced Functional Materials, 21 (2011) 434-440.

* cited by examiner

SEQUENCE LISTING

<160> NUMBER OF SEQ ID NOS: 24

<210> SEQ ID NO 1
<211> LENGTH: 7
<212> TYPE: PRT
<213> ORGANISM: Artificial
<220> FEATURE:
<223> OTHER INFORMATION: Derivative of Homo sapiens plasminogen kringle
      5 protein

<400> SEQUENCE: 1

Gly Val Ile Thr Arg Ile Arg
1               5

<210> SEQ ID NO 2
<211> LENGTH: 4
<212> TYPE: PRT
<213> ORGANISM: Artificial
<220> FEATURE:
<223> OTHER INFORMATION: Arginiine-rich tetrapeptide

<400> SEQUENCE: 2

Arg Arg Ser Arg
1

<210> SEQ ID NO 3
<211> LENGTH: 7
<212> TYPE: PRT
<213> ORGANISM: Artificial
<220> FEATURE:
<223> OTHER INFORMATION: Derivative of Homos sapiens protamine protein

<400> SEQUENCE: 3

Arg Arg Ser Ser Arg Arg Trp
1               5

<210> SEQ ID NO 4
<211> LENGTH: 5
<212> TYPE: PRT
<213> ORGANISM: Artificial
<220> FEATURE:
<223> OTHER INFORMATION: Derivative of Homo sapiens Pigment
      Epithelium-Derived Factor Peptide

<400> SEQUENCE: 4

Tyr Arg Val Arg Ser
1               5

<210> SEQ ID NO 5
<211> LENGTH: 5
<212> TYPE: PRT
<213> ORGANISM: Artificial
<220> FEATURE:
<223> OTHER INFORMATION: Derivative of Homo sapiens alpha-crystallin and
      heat shock protein 20

<400> SEQUENCE: 5

Arg Arg Tyr Arg Leu
1               5

<210> SEQ ID NO 6
<211> LENGTH: 8
<212> TYPE: PRT
<213> ORGANISM: Artificial
<220> FEATURE:
<223> OTHER INFORMATION: Derivative of Homo sapiens Pigment
      Epithelium-Derived Factor Peptide

```
<400> SEQUENCE: 6

Tyr Asn Leu Tyr Arg Val Arg Ser
1               5

<210> SEQ ID NO 7
<211> LENGTH: 6
<212> TYPE: PRT
<213> ORGANISM: Artificial
<220> FEATURE:
<223> OTHER INFORMATION: Derivative of Homo sapiens plasminogen kringle
      5 protein

<400> SEQUENCE: 7

Val Ile Thr Arg Ile Arg
1               5

<210> SEQ ID NO 8
<211> LENGTH: 5
<212> TYPE: PRT
<213> ORGANISM: Artificial
<220> FEATURE:
<223> OTHER INFORMATION: Derivative of Homo sapiens Pigment
      Epithelium-Derived Factor Peptide

<400> SEQUENCE: 8

Leu Tyr Arg Val Arg
1               5

<210> SEQ ID NO 9
<211> LENGTH: 6
<212> TYPE: PRT
<213> ORGANISM: Artificial
<220> FEATURE:
<223> OTHER INFORMATION: Derivative of Homo sapiens protamine protein

<400> SEQUENCE: 9

Arg Arg Ser Ser Arg Arg
1               5

<210> SEQ ID NO 10
<211> LENGTH: 7
<212> TYPE: PRT
<213> ORGANISM: Artificial
<220> FEATURE:
<223> OTHER INFORMATION: Derivative of Homo sapiens Pigment
      Epithelium-Derived Factor Peptide

<400> SEQUENCE: 10

Leu Tyr Arg Val Arg Ser Ser
1               5

<210> SEQ ID NO 11
<211> LENGTH: 7
<212> TYPE: PRT
<213> ORGANISM: Artificial
<220> FEATURE:
<223> OTHER INFORMATION: Derivative of Homo sapiens plasminogen kringle
      5 protein

<400> SEQUENCE: 11

Gly Val Ile Thr Arg Ile Arg
1               5

<210> SEQ ID NO 12
<211> LENGTH: 10
<212> TYPE: PRT
<213> ORGANISM: Artificial
```

```
<220> FEATURE:
<223> OTHER INFORMATION: Derivative of Homo sapiens protamine protein

<400> SEQUENCE: 12

Ser Gly Gly Gly Tyr Arg Ala Arg Pro Ala
1               5                   10

<210> SEQ ID NO 13
<211> LENGTH: 7
<212> TYPE: PRT
<213> ORGANISM: Artificial
<220> FEATURE:
<223> OTHER INFORMATION: Derivative of Homo sapiens plasminogen kringle
      5 protein

<400> SEQUENCE: 13

Gly Gly Tyr Arg Ala Arg Pro
1               5

<210> SEQ ID NO 14
<211> LENGTH: 6
<212> TYPE: PRT
<213> ORGANISM: Artificial
<220> FEATURE:
<223> OTHER INFORMATION: Derivative of Homo sapiens fibrin protein

<400> SEQUENCE: 14

Gly Tyr Arg Ala Arg Pro
1               5

<210> SEQ ID NO 15
<211> LENGTH: 8
<212> TYPE: PRT
<213> ORGANISM: Artificial
<220> FEATURE:
<223> OTHER INFORMATION: Derivative of Homo sapiens heat shock protein
      20

<400> SEQUENCE: 15

Pro His Arg Arg Tyr Arg Leu Pro
1               5

<210> SEQ ID NO 16
<211> LENGTH: 10
<212> TYPE: PRT
<213> ORGANISM: Artificial
<220> FEATURE:
<223> OTHER INFORMATION: Derivative of Homo sapiens protamine protein

<400> SEQUENCE: 16

Pro Arg Arg Arg Arg Ser Ser Ser Arg Pro
1               5                   10

<210> SEQ ID NO 17
<211> LENGTH: 7
<212> TYPE: PRT
<213> ORGANISM: Artificial
<220> FEATURE:
<223> OTHER INFORMATION: Derivative of Homo sapiens fibrin protein

<400> SEQUENCE: 17

Arg Arg Ser Ser Ser Arg Pro
1               5

<210> SEQ ID NO 18
<211> LENGTH: 6
<212> TYPE: PRT
```

-continued

```
<213> ORGANISM: Artificial
<220> FEATURE:
<223> OTHER INFORMATION: Derivative of Homo sapiens protamine protein

<400> SEQUENCE: 18

Pro Arg Arg Arg Arg Ser
1               5

<210> SEQ ID NO 19
<211> LENGTH: 4
<212> TYPE: PRT
<213> ORGANISM: Artificial
<220> FEATURE:
<223> OTHER INFORMATION: Derivative of Homo sapiens protamine protein

<400> SEQUENCE: 19

Arg Arg Ser Arg
1

<210> SEQ ID NO 20
<211> LENGTH: 10
<212> TYPE: PRT
<213> ORGANISM: Artificial
<220> FEATURE:
<223> OTHER INFORMATION: Derivative of Homo sapiens fibrin pnotein

<400> SEQUENCE: 20

Pro Ile Ser Gly Gly Gly Tyr Arg Ala Arg
1               5                   10

<210> SEQ ID NO 21
<211> LENGTH: 10
<212> TYPE: PRT
<213> ORGANISM: Homo Sapiens

<400> SEQUENCE: 21

Gly Asp Gly Val Ile Thr Arg Ile Arg Leu
1               5                   10

<210> SEQ ID NO 22
<211> LENGTH: 4
<212> TYPE: PRT
<213> ORGANISM: Artificial sequence
<220> FEATURE:
<223> OTHER INFORMATION: Synthetic peptide

<400> SEQUENCE: 22

Ile Thr Arg Trp
1

<210> SEQ ID NO 23
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = sarcosine

<400> SEQUENCE: 23

Xaa Leu Tyr Arg Val Arg Ser Ser
1               5

<210> SEQ ID NO 24
<211> LENGTH: 5
```

```
<212> TYPE: PRT
<213> ORGANISM: Artificial sequence
<220> FEATURE:
<223> OTHER INFORMATION: Synthetic peptide

<400> SEQUENCE: 24

Tyr Arg Ala Arg Pro
1               5
```

NANOCARRIERS HAVING SURFACE CONJUGATED PEPTIDES AND USES THEREOF FOR SUSTAINED LOCAL RELEASE OF DRUGS

STATEMENT REGARDING FEDERALLY SPONSORED RESEARCH OR DEVELOPMENT

This invention was made with government support under R24 EY022883 (University of Wisconsin Subcontract to Northwestern University, #457K273) awarded by the National Institutes of Health. The government has certain rights in the invention.

STATEMENT REGARDING SEQUENCE LISTING

The text of the computer readable sequence listing filed herewith, titled "35569-202_SEQUENCE-_LISTING_ST25", created Sep. 19, 2019, having a file size of 5,000 bytes, is hereby incorporated by reference in its entirety.

CROSS-REFERENCE TO RELATED PATENT APPLICATIONS

This application claims the benefit of priority to U.S. Provisional Application No. 62/420,344, filed on Nov. 10, 2016, the content of which is incorporated herein by reference in its entirety. This application also is a continuation-in-part of U.S. patent application Ser. No. 15/497,822, filed on Apr. 26, 2017, which application claims the benefit of priority to U.S. Provisional Application No. 62/327,767, filed on Apr. 26, 2016, the contents of which are incorporated herein by reference in their entireties.

BACKGROUND

The field of the invention relates to compositions and methods for localized and sustained delivery of drugs when it is desirable to keep the drugs confined to a specific body space to enhance their therapeutic action and minimize cost and non-essential exposure. In particular, the field of the invention relates to compositions and methods for localized and sustained delivery of water-soluble synthetic compounds, as well as synthetic lipophilic compounds typically <1,000 Mol. Wt., as well as localized and sustained delivery of larger hydrophilic therapeutic agents such as peptides, proteins and nucleic acids.

Major blinding diseases such as exudative "wet" macular degeneration (AMD), and diabetic retinopathy are caused by excessive pathologic capillary sprouting beneath the retina, damaging retinal layers above. Anti-angiogenic proteins including Avastin, Lucentis and Eyelea, all of which neutralize angiogenic VEGF, slow progress of neovascular eye disease, but must be injected into patient vitreous humor (VH). VH fills most of the eye, is viscous and contains natural polymers with multiple negative charges. Therapeutic proteins move through and out of the eye with half-lives of 4-8 days, they must be re-injected at 1-2 month intervals to sustain efficacy. Frequent injection is a great clinical burden, is painful, and increases risk of retinal detachment and infection. Nano-technology involving entrapment or binding of the proteins into transparent degradable particles has been attempted by many labs seeking continuous release of the injected agent to decrease injection frequency, an approach also applied to small synthetic drugs. Typical carriers are large particles (>1 micron), are difficult to sterilize), they move slowly through viscous ocular fluid, or may be smaller and anchored via stable multi (+)charges. Particles may exit the eye intact or may break down to yield fragments which can be toxic or inflammatory, none has yet been approved for the delivery of proteins or peptides.

SUMMARY

Disclosed are biodegradable nanocarriers having a net positive surface charge and zeta potential between about +2 to about +20 mV. The positive surface charge of the nanocarriers is provided by peptides that are covalently attached to the surface of the nanocarriers for use as anchoring peptides. The nanocarriers may comprise a non-peptide drug, contained within the carrier, or a peptide drug linked to the carrier simultaneously with the anchoring peptides and may be administered for localized and sustained delivery of the drug. The anchoring peptides themselves also may include therapeutic peptides, when these are positively charged through L-Arg content, and attached through metastable bonds. Preferably, the anchoring peptides are relatively short containing less than about 12 amino acids, safe and non-toxic, non-immunogenic, with net positive charges contributed by 2-4 L-arginine residues present in each of the anchoring peptides.

The disclosed biodegradable nanocarriers having a net positive surface charge and zeta potential between about +2 to about +20 mV adhere to poly-anionic carbohydrates when injected in vivo and thus diffuse slowly from their injection site. As such, the biodegradable nanocarriers may be injected into tissues comprising poly-anionic carbohydrates, such as vitreous humor or other tissues, and the biodegradable nanocarriers will exhibit slow diffusion from the injected tissue.

The anchor peptides of the biodegradable nanocarriers may be attached to hydroxyl groups present on the surface of the biodegradable nanocarriers via stable carbamate, leading to slowed diffusion, through multiple ionic interactions, in physiological spaces rich in poly-anionic carbohydrates (e.g. hyaluronic acid or sulfated polysaccharides such as heparinoids, in vitreous humor or other tissue). Alternatively, the peptides, linked as above, may also contain a metastable bridge formed through an amino alcohol which is esterified to a dicarboxylic acid appended to the peptides at their N-terminus. Preferably, the ester bond between the amino alcohol and the dicarboxylic acid spontaneously hydrolyzes to break down at predictable rates over many weeks or months, which allows the biodegradable nanocarriers, which can be eliminated or biodegraded, to diffuse from injected tissue more rapidly after most anchoring peptides are lost through hydrolysis of the ester bond. The rate of this hydrolysis process can be used to tune drug release of a drug that is linked to the nanocarriers via the peptide, by selecting various amino-alcohols and dicarboxylic acids for forming the ester bond. As such, the disclosed nanocarriers may be utilized for administering intra-ocular therapeutics and achieving continuous ocular delivery of both therapeutic proteins and smaller molecules, within or attached to the biodegradable nanocarriers, thus extending time between intra-ocular injections.

DETAILED DESCRIPTION

Figure 1:
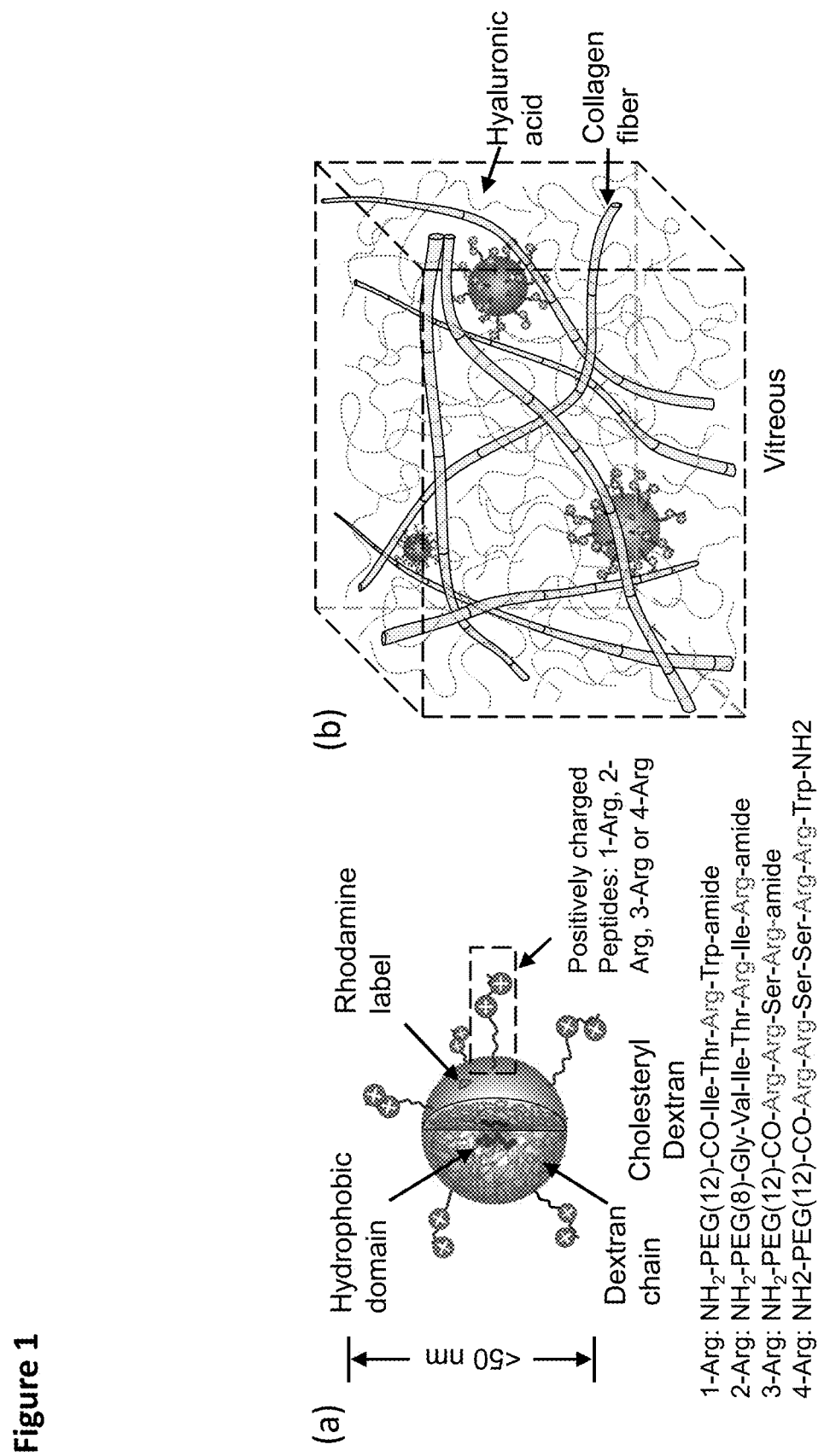
FIG. 1. Schematic drug delivery mechanism. (a) Illustration of particle structure. Cholesteryl dextran nanoparticle (less than 50 nm in diameter). Hydrophobic domains are inside the particle close to the core. Particle is illustrated as being labeled by a Rhodamine B amine tracking dye with a density of about 2 molecules per particle. Four types of positively charged peptides (1-Arg: SEQ ID NO:22; 2-Arg SEQ ID NO:1; 3-Arg SEQ ID NO:2; 4-Arg SEQ ID NO: 3) are illustrated as being linked on the particle surface, with a density of about 20 to about 80 peptides per particle. (b) Illustration of particles within vitreous humor. Vitreous humor is a transparent aqueous gel containing a highly cross-linked collagen fiber-hyaluronic acid (HA). HA molecules are anionic, with random coil structure, fills the space between collagen fibers to prevent aggregation. Nanoparticles (NP) are immobilized by the ionic binding between peptides anchored on the particle surface (circles) and hyaluronic acid molecules (strands) in vitreous humor.

The present invention is described herein using several definitions, as set forth below and throughout the application.

Unless otherwise specified or indicated by context, the terms "a", "an", and "the" mean "one or more." For example, "a nanocarrier" and "a peptide" should be interpreted to mean "one or more. nanocarriers" and "one or more peptides," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein, a "patient" may be interchangeable with "subject" or "individual" and means an animal, which may be a human or non-human animal, in need of treatment. Non-human animals may include dogs, cats, horses, cows, pigs, sheep, and the like.

A "patient in need thereof" may include a patient having or at risk for developing an eye disease. The presently disclosed peptides, prodrugs, and pharmaceutical compositions may be utilized to treat eye diseases that are characterized by neovascular retinal disease, such as macular degeneration, and that may be treated with anti-angiogenic agents. The presently disclosed peptides, prodrugs, and pharmaceutical compositions may be utilized to treat eye diseases such as diabetic retinopathy. The presently disclosed peptides, prodrugs, and pharmaceutical compositions may be utilized to treat eye diseases by administering peptide, or non-peptide drugs or prodrugs by intravitreal injection of the disclosed peptide-anchored carriers.

A "patient in need thereof" may include a patient having macular degeneration. Macular degeneration is a medical condition predominantly found in elderly adults in which the center of the retina of the eye, otherwise known as the "macula" area of the retina, exhibits thinning, atrophy, and sometimes new blood vessel formation. Although macular degeneration sometimes may affect younger individuals, the term generally refers to "age-related" macular degeneration (i.e., "AMD" or "ARMD"). Advanced AMD has two forms referred to as the "dry" and "wet" forms. The dry form of advanced AMD is characterized by central geographic atrophy, which causes vision loss through the loss of photoreceptors in the central part of the eye (i.e., rods and cones). The wet form of advanced AMD, otherwise referred to as "neovascular" or "exudative" AMD, causes vision loss due to abnormal blood vessel growth in the choriocapillaris, through a retinal layer referred to as "Bruch's membrane." The wet form of AMD ultimately leads to blood and protein leakage below the macula. This bleeding, leaking, and scarring below the macula eventually cause irreversible damage to the photoreceptors and rapid vision loss if left untreated. Until recently, no effective treatments were known for wet macular degeneration. However, new drugs that inhibit angiogenesis (i.e., "anti-angiogenic agents") have been shown to cause regression of the abnormal blood vessels and improvement of vision. In order to be effective, anti-angiogenic agents must be injected directly into the vitreous humor of the eye. The duration of effectiveness of such injections is impractically short for small peptides unless the latter are continuously released from a carrier macromolecule, or nanocarrier, for which ester linkage provides controlled rates of release.

The compositions disclosed herein may include nanocarriers. As used herein, the term "nanocarrier" may be used interchangeably with the terms "nanoparticle" and "nanoparticle carrier" and may refer to a solid particle, a semi-solid particle and/or a colloidal particle (e.g., a gel or hydrogel). The nanocarriers disclosed herein preferably have an effective diameter of less than about 1 micron, 900 nm, 800 nm, 700 nm, 600 nm, 500 nm, 400 nm, 300 nm, 200 nm, 100 nm or less, or the nanocarriers have an effective diameter within a range bounded by any of these values (e.g., 5-50 nm or 100-200 nm).

The disclosed nanocarriers preferably are transparent, for example as measured by total transmittance for use in the eye. Preferably, the nanocarriers disclosed herein may absorb and reflect less than about 10%, 9%, 8%, 7%, 6%, 5%, 4%, 3%, 2%, or 1% of incident light and/or may have a total transmittance of at least about 90%, 91%, 92%, 93%, 94%, 95%, 96%, 97%, 98%, or 99% of incident light. As such, the nanocarriers disclosed herein may comprise a polymeric material that absorbs and reflects less than about 10%, 9%, 8%, 7%, 6%, 5%, 4%, 3%, 2%, or 1% of incident light and/or has a total transmittance of at least about 90%, 91%, 92%, 93%, 94%, 95%, 96%, 97%, 98%, or 99% of incident light. Preferably, the nanocarriers remain transparent after the nanocarriers are injected into the vitreous humor. Transparency may not be required for use outside the eye.

The disclosed nanocarriers preferably are biodegradable and/or can be safely eliminated through the kidney or alimentary tract. As used herein, "biodegradable" describes a material, such as a polymer, that is capable of being degraded in a physiological environment into smaller basic components. Preferably, the smaller basic components are innocuous. For example, a biodegradable polymer may be degraded into basic components that include, but are not limited to, water, carbon dioxide, sugars, organic acids (e.g., tricarboxylic or amino acids), and alcohols (e.g., glycerol or polyethylene glycol). Biodegradable materials may include polymeric carbohydrates. Biodegradable materials (including polymers) that may be utilized to prepare the nanocarriers contemplated herein may include materials disclosed in U.S. Pat. Nos. 7,470,283; 7,390,333; 7,128,755; 7,094,260; 6,830,747; 6,709,452; 6,699,272; 6,527,801; 5,980,551; 5,788,979; 5,766,710; 5,670,161; and 5,443,458; and U.S. Published Application Nos. 20090319041; 20090299465; 20090232863; 20090192588; 20090182415; 20090182404; 20090171455; 20090149568; 20090117039; 20090110713; 20090105352; 20090082853; 20090081270; 20090004243; 20080249633; 20080243240; 20080233169; 20080233168; 20080220048; 20080154351; 20080152690; 20080119927; 20080103583; 20080091262; 20080071357; 20080069858; 20080051880; 20080008735; 20070298066; 20070288088; 20070287987; 20070281117; 20070275033; 20070264307; 20070237803; 20070224247; 20070224244; 20070224234; 20070219626; 20070203564; 20070196423; 20070141100; 20070129793; 20070129790; 20070123973; 20070106371; 20070050018; 20070043434; 20070043433; 20070014831; 20070005130; 20060287710; 20060286138; 20060264531; 20060198868; 20060193892; 20060147491; 20060051394; 20060018948; 20060009839; 20060002979; 20050283224; 20050278015; 20050267565; 20050232971; 20050177246; 20050169968; 20050019404; 20050010280; 20040260386; 20040230316; 20030153972; 20030153971; 20030144730; 20030118692; 20030109647; 20030105518; 20030105245; 20030097173; 20030045924; 20030027940; 20020183830; 20020143388; 20020082610; and 0020019661; the contents of which are incorporated herein by reference in their entireties. Materials that may be safely eliminated through the kidney may include, but are not limited to, dextran 40 and dextran 70.

As used herein, the term "peptide" refers to a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine (sarcosine), 2-Aminoisobutyric acid, N-methyl-2-aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. Typically, the amide linkages of the peptides are formed from an amino group of the backbone of one amino acid and a carboxyl group of the backbone of another amino acid.

In some embodiments, the disclosed peptides may comprise two or more amino acids which optionally may be charged or uncharged at physiological pH. Typically, positively charged amino acids of the peptide at physiological pH include, L-arginine, and lysine, with partial + charge found in histidine. Typically, negatively charged amino acids at physiological pH include aspartic acid and glutamic acid. The remaining amino acids, other than these positively charged and negatively charged amino acids, typically are neutral at physiological pH. L-arginine is the predominant or sole source of charge in anchor peptides used here. The minimum net charge of each our peptides, when covalently linked to carrier is +2, the maximum net charge of each being +4.

As used herein, a peptide is defined as a short polymer of amino acids, of a length typically of 20 or less amino acids, and more preferred is a length of less than 12 amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length ≥100 amino acids (Garrett & Grisham, Biochemistry, $2^{nd}$ edition, 1999, Brooks/Cole, 110). Peptides or protein agents to be delivered may simultaneously be attached on the carriers to which the smaller anchoring peptides are conjugated.

The peptides disclosed herein may be modified to include non-amino acid moieties. Modifications may include but are not limited to carboxylation (e.g., N-terminal carboxylation via addition of a di-carboxylic acid having 4-8 straight-chain or branched carbon atoms, such as glutaric acid, succinic acid, adipic acid, suberic acid and 4,4-dimethylglutaric acid), amidation (e.g., C-terminal amidation via addition of an amide or substituted amide such as alkylamide or dialkylamide), PEGylation, including amino-PEGylation (e.g., N-terminal or C-terminal PEGylation via amide bonds), acylation (e.g., N-acylation (amides) with alpha, beta, gamma, delta, or epsilon amino acids. In addition, N-terminal amino-PEG-peptide may be further capped as an amino-PEG amide with 3-pyrrolidine carboxylic acid or 3-pyrrolidyine-amido-succininc acid whereby the appended pyrrolidine amino group can form the carbamate link to dextran OH groups.

The disclosed peptides may exhibit one or more biological functions including anti-angiogenic activity. Methods for measuring anti-angiogenic activity are disclosed herein and are known in the art.

The disclosed peptides may be synthesized by any technique known to those of skill in the art and by methods as disclosed herein. Methods for synthesizing the disclosed peptides may include chemical synthesis of proteins or peptides, the expression of peptides through standard molecular biological techniques, and/or the isolation of proteins or peptides from natural sources. The disclosed peptides thus synthesized may be subject to further chemical and/or enzymatic modification. Various methods for commercial preparations of peptides and polypeptides are known to those of skill in the art.

Reference is made herein to peptides, polypeptides and pharmaceutical compositions comprising peptides and polypeptides. Exemplary peptides and polypeptides may comprise, consist essentially of, or consist of the amino acid sequence of any of SEQ ID NOs:1-20, or variants of the peptides and polypeptides may comprise, consist essentially of, or consist of an amino acid sequence having at least about 80%, 90%, 95%, 96%, 97%, 98%, or 99% sequence identity to any of SEQ ID NOs:1-20. Variant peptides polypeptides may include peptides or polypeptides having one or more amino acid substitutions, deletions, additions and/or amino acid insertions relative to a reference peptide or polypeptide. Preferably, in order to minimize immunogenicity and toxicity, anchoring peptides utilized here are small (<12 amino acids), and contain no fewer than 2 L-Arg and no more than 4 L-Arg in which the amino acid sequence is identical to or closely resembles naturally occurring human protein sequences found in intercellular matrix or in body fluids such as urine or plasma. Thus no more than one amino acid internally and no more than one N-terminal appended amino acid typically varies from the natural human sequence.

The amino acid sequences contemplated herein may include conservative amino acid substitutions relative to a reference amino acid sequence. For example, a variant peptide or polypeptide as contemplated herein may include conservative amino acid substitutions relative to a reference peptide or polypeptide. "Conservative amino acid substitutions" are those substitutions that are predicted to interfere least with the properties of the reference polypeptide. In other words, conservative amino acid substitutions substantially conserve the structure and the function of the reference protein. The following table provides a list of exemplary conservative amino acid substitutions.

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Gln | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the peptide or polypeptide backbone in the area of the substitution, for example, as a beta sheet or alpha helical conformation, (b) the charge or hydrophobicity of the molecule at the site of the substitution, and/or (c) the bulk of the side chain.

Variants comprising deletions relative to a reference amino acid sequence are contemplated herein. A "deletion" refers to a change in the amino acid or nucleotide sequence that results in the absence of one or more amino acid residues or nucleotides relative to a reference sequence. A deletion may remove at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

A "variant" of a particular polypeptide sequence may be defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" may have substantially the same functional activity as a reference polypeptide. For example, a variant may exhibit or more biological activities associated with PEDF. "Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

A "composition comprising a given polypeptide" refers broadly to any composition containing the given amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components (e.g., Denhardt's solution, dry milk, salmon sperm DNA, and the like).

The disclosed pharmaceutical composition may comprise the disclosed peptides, polypeptides, and variants at any suitable dose. Suitable doses may include, but are not limited to, about 0.01 µg/dose, about 0.05 µg/dose, about 0.1 µg/dose, about 0.5 µg/dose, about 1 µg/dose, about 2

µg/dose, about 3 µg/dose, about 4 µg/dose, about 5 µg/dose, about 10 µg/dose, about 15 µg/dose, about 20 µg/dose, about 25 µg/dose, about 30 µg/dose, about 35 µg/dose, about 40 µg/dose, about 45 µg/dose, about 50 µg/dose, about 100 µg/dose, about 200 µg/dose, about 500 µg/dose, or about 1000 µg/dose. In some embodiments, these contemplated doses may be administered intravitreally, intracranially, and/or intraperitoneally.

The disclosed peptides, polypeptides, or variants thereof may be administered at any suitable dose level. In some embodiments, a subject in need thereof is administered a peptide, polypeptide, or variant thereof at a dose level of from about 1 ng/kg up to about 1 mg/kg. In some embodiments, the peptide, polypeptide, or variant thereof is administered to the subject in need thereof at a dose level of at least about 1 ng/kg, 2 ng/kg, 5 ng/kg, 10 ng/kg, 20 ng/kg, 50 ng/kg, 100 ng/kg, 200 ng/kg, 500 ng/kg, 1 µg/kg, 2 µg/kg, 5 µg/kg, 10 µg/kg, 20 µg/kg, 50 µg/kg, 100 µg/kg, 200 µg/kg, 500 µg/kg, or 1 mg/kg. In other embodiments, the peptide, polypeptide, or variant thereof is administered to the subject in need thereof at a dose level of less than about 1 mg/kg, 500 µg/kg, 200 µg/kg, 100 µg/kg, 50 µg/kg, 20 µg/kg, 10 µg/kg, 5 µg/kg, 2 µg/kg, 1 µg/kg, 500 ng/kg, 200 ng/kg, 100 ng/kg, 50 ng/kg, 20 ng/kg, 10 ng/kg, 5 ng/kg, 2 ng/kg, or 1 ng/kg. In further embodiments, the peptide, polypeptide, or variant thereof is administered to a subject in need thereof within a dose level range bounded by any 1 ng/kg, 2 ng/kg, 5 ng/kg, 10 ng/kg, 20 ng/kg, 50 ng/kg, 100 ng/kg, 200 ng/kg, 500 ng/kg, 1000 ng/kg, 2000 ng/kg, or 5000 ng/kg.

The disclosed peptides, polypeptides, or variants thereof may be administered under any suitable dosing regimen. Suitable dosing regimens may include, but are not limited to, once every week, once every month, once every two months, once every three months, once every four months, once every 5 months, or once every 6 months.

The peptides and prodrugs utilized in the methods disclosed herein may be formulated as a pharmaceutical composition for delivery via any suitable route (e.g. parenteral or intravitreal routes). As such, pharmaceutical compositions comprising the peptides and prodrugs may be adapted for administration by any appropriate route, for example intravitreal or intraperitoneal, or intracranial or intra-articular with the intention of local confinement, and parenteral (including subcutaneous, intramuscular, intravenous or intradermal) route. Such formulations may be prepared by any method known in the art of pharmacy, for example by bringing into association the active ingredient with suitable carrier(s) or excipient(s). In some embodiments, the prodrug carrier-bound forms described herein may be intended for less frequent dosing ranging from once weekly to once monthly to once per 2 months or less frequently. Pharmaceutical compositions adapted for parenteral administration include aqueous and non-aqueous sterile injection solutions which may contain anti-oxidants, buffers, bacteriostats and solutes which render the formulation isotonic with bodily fluid of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Formulations may contain excess hyaluronic acid or other naturally occurring poly-anionic carbohydrates as excipients intended to immobilize and slow diffusion of the cationic nanoparticles, to minimize toxicity and extend continuous release.

The nanocarriers disclosed herein may be formulated as pharmaceutical compositions for use in treating and/or preventing diseases or disorders that are amenable to treatment by anti-angiogenic agents. As such, the pharmaceutical compositions may be administered to a patient in order to inhibit angiogenesis.

The disclosed methods may include administering to a patient an effective amount of a pharmaceutical composition to treat and/or prevent a disease and/or disorder. As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

The disclosed methods may include administering to a patient an effective amount of a pharmaceutical composition for inhibiting angiogenesis relative to a control. In some embodiments, angiogenesis and/or tumorigenesis is inhibited by at least 10%, at least 25%, at least 50%, at least 75%, at least 90%, or at least 95% in a treated sample relative to an untreated control sample.

Nanocarriers Having Surface Conjugated Peptides and Uses Thereof for Sustained Local Release of Drugs Disclosed are nanocarriers that are biodegradable, that are transparent, that have an average effective diameter of less than about 200 nm (preferably between 5-50 nm) and that have a net positive surface charge and zeta potential between about +2 to about +9, +10, +11, +12, +13, +14, +15, +16, +17, +18, +19, or +20 mV. The positive surface charge of the nanocarriers is provided by peptides that are covalently attached to the surface of the nanocarriers. Larger zeta potential (up to +20 mV) may be used for confinement in body cavities having lower concentrations of poly-anionic carbohydrate than found in vitreous, or in more liquefied geriatric vitreous, or where purified hyaluronic acid (HA) is used as a medium (formulation) for the delivery of peptide-conjugated carriers.

In some embodiments, the nanocarriers may include a core comprising a polymeric carbohydrate material. Suitable materials for the nanocarriers may include, but are not limited to, dextran which optionally is a condensed dextran hydrogel, chitosan, pullulan, or a dendrimer. The core material of the nanocarriers preferably includes hydroxyl groups and/or carboxyl groups on the surface of the core material of the nanocarriers. In some embodiments, the nanocarriers comprise dendrimers having terminal hydroxyl groups and/or terminal carboxyl groups. In further embodiments, the carriers comprise dextran and/or hyaluronic acid, and optionally the dextran or hyaluronic acid is crosslinked and/or condensed. Nanoparticulate carriers as disclosed in the art, in some instances, may be modified to prepare nanocarriers as disclosed herein. (See, e.g., Araujo et al., Nanomedicine 8 (2012) 1034-1041; Park et al., Diabetes 58 (2009) 1902-1913; Jin et al., Inest. Ophthalmol. Vis. Sci. 52 (2011) 6230-6237; Liu et al., Invest Ophthalmol. Vis. Sci. 52 (2011) 4789-4794; Pepic et al., J. Pharm. Sci. 99 (2010) 4317-4325; Marano et al., Gen Ther. 12 (2005) 1544-1550; and Marano et al., Exp. Eye Res. 79 (2004) 525-535; the contents of which are incorporated herein by reference in their entireties). Polylactide (PLA) nanocarriers, poly (lactic-co-glycolic acid) (PLGA) nanocarriers, PLA/PLGA nanocarriers, and derivatives thereof may be modified to prepare nanocarriers as contemplated herein. Polyamidoamine (PAMAM) dendrimer nanocarriers and derivatives thereof may be modified to prepare nanocarriers as contemplated herein. Dextran nanocarriers, derivatives thereof, and hydrogels thereof may be modified to prepare nanocarriers as contemplated herein. Cholesterol-modified or lipid-modified dextran and hydrogels thereof may be modified to prepare nanocarriers as contemplated herein (e.g., dextran polymers to which cholesterol or stearic amine has been conjugated to 0.5%, 1%, 2%, 3%, 4%, 5%, 6%, 7%, 8%, 9%, or 10% (or a percentage range bounded by any of 0.5%, 1%, 2%, 3%, 4%, 5%, 6%, 7%, 8%, 9%, or 10%) of the sugar monomers of dextran). In nanocarriers comprising cholesterol-modified dextran, preferably the attached cholesterol forms a core, thereby condensing the dextran polymer into a compact sphere. A cholesterol core may be substituted by other lipohilic compounds such as stearylamine. Such particle cores, in addition to making the carriers more compact, may be used to contain synthetic lipophilic drugs for delivery, while surface-linked peptides prolong overall intravitreal residence.

The disclosed nanocarriers include peptides conjugated to the surface of the nanocarriers. The disclosed peptides typically are small and comprise at least 2 amino acids and no more than 11 amino acids. In some embodiments, the disclosed nanocarriers comprise at least 5, 10, 15, 20, 25, 30, 40, 50, 60, 70 or 80 peptides per 70-100 kD nanocarrier (or the nanocarriers comprise a range of peptides bounded by any of 5, 10, 15, 20, 25, 30, 40, 50, 60, 70 or 80 peptides per particle (e.g., 15-35 peptides per nanocarrier)) where the full sized carrier-peptide conjugate has molecular weight ranging from 20 kD to 200 kD.

The disclosed peptides may comprise an amino acid sequence that is selected in order to provide a suitable surface charge to the nanocarriers to which the peptides are conjugated. In some embodiments, the amino acid sequence of the peptides includes at least 2 L-Arginine residues, no more than 4 L-Arginine residues, and preferably no other charged amino acids other than L-Arginine residues, excluding amines that may be used in linking the peptides to the nanocarriers. As such, the peptides may provide a positive net charge to the surface of the nanocarriers.

The disclosed peptides may comprise an amino acid sequence that is selected in order to minimize any immune response against the peptides. In some embodiments, the disclosed peptides may comprise an amino acid sequence that is found in a human protein. In some embodiments, the disclosed peptides comprise an amino acid sequence of a human protein that is secreted into the extracellular matrix or that is found in vitreous humor, blood, urine, or saliva. Suitable amino acid sequences for the disclosed peptides may include, but are not limited to, amino acid sequences found in human thrombospondin, pigment epithelium-derived factor (PEDF), alpha A crystallin, heat shock protein 20, laminin receptor, circulating fibrin peptides, and protamines. To further minimize immunogenicity or instability PEG amines from molecular weight 200 to 2000 may be appended as amides to the C-termini of anchoring peptides, or amino-PEG-carboxylates may be appended to the peptide as N-terminal amides, so that N-terminal amino groups can be linked, as carbamates or amides to the carrier surface to shield anchoring peptides from the immune system or from degradative enzymes.

In some embodiments, the disclosed peptides may comprise an amino acid sequence of pigment epithelium-derived factor (PEDF) or a modified amino acid sequence of PEDF. Modified PEDF peptides that may be suitable for use in the present application may include modified PEDF peptides disclosed in U.S. Published Application No. 2017-0305998, published on Oct. 26, 2017, the content of which is incorporated herein by reference in its entirety.

The disclosed peptides may be modified. In some embodiments, the disclosed peptides have C-terminal amide or ethylamide groups, PEG(4-12)-amide groups, or 3-pyrrolidine-carboxamido-PEG(4-12) groups.

The disclosed peptides may be further modified to include a non-naturally occurring amino acid at their N-terminus. In some embodiments, the peptides include at their N-terminus a neutral amino acid residue selected from the group consisting of sarcosine, beta-alanine, 2-amino-isobutyric acid or N-methyl-2-aminoisobutyric acid. The disclosed peptides also may contain between 1 and 2 modified amino acids internally, provided that the overall sequence is at least 75% identical to that within a human protein.

The disclosed peptides typically are covalently conjugated to a hydroxyl group present on the surface of the nanocarriers. In some embodiments, the peptides are covalently attached to the nanocarriers via conjugation between hydroxyl groups on the surface of the nanocarriers and free amino groups on the peptides. Suitable amino groups on the peptides for covalent attachment may include, but are not limited to free alpha amino groups on the peptides, free beta amino groups on the peptides, or free amino groups present in an N-terminal moiety of the peptides, such as a linker moiety which may be referred to as "B." Optionally, linker B is selected from the group consisting of amino-n-butoxy, amino-ethoxyethyloxy, amino-piperidyl (3, or 4)-oxy, amino-pyrrolidinyl (3)-oxy, amino-benzyl (3, or 4)-oxy, aminoethylamido-valeric acid (4)-oxy, amino-cyclohexyl (3, or 4)-oxy, and amino-cyclopentyl (3)-oxy. Suitable amino groups may be present in an N-terminal moiety of the peptides, such as an amino-PEG-acyl group, or an epsilon amino caproyl group.

In some embodiments, the peptides of the disclosed nanocarriers may have a formula: B-Z-AA0-AA1-AA2-AA3-AA4-AA5-AA6-AA7-AA8-AA9-AA10-Y, wherein: B is present or absent, and when B is present, B is selected from the group consisting of amino-n-butoxy, amino-ethoxyethyloxy, amino-piperidyl (3, or 4)-oxy, amino-pyrrolidinyl (3)-oxy, amino-benzyl (3, or 4)-oxy, aminoethylamido-valeric acid (4)-oxy, amino-cyclohexyl (3, or 4)-oxy, and amino-cyclopentyl (3)-oxy; Z is absent or present, and when Z is present, Z is amino-PEG-carboxylic acid (optionally including 4-16 ethylene glycol units) in amide bond to AA0 or AA1; AA0 is present or absent, and when present, AA0 is selected from the group consisting of L-arginine, a naturally occurring amino acid with an uncharged side chain (e.g., sarcosine and glycine), and beta-alanine; AA1, AA2, AA3, AA4, AA5, AA6, AA7, AA8, AA9, and AA10 each individually are present or absent, and when present are individually selected from L-arginine or a naturally occurring amino acid with an uncharged side chain; Y is an amide, a mono-substituted or di-substituted alkyl amide (e.g., methylamide, ethylamide, and dimethylamide), or a PEG(4-12) amide; with the proviso that: the peptides have a net positive charge and zeta potential between about +2 to about +9, +10, +11, +12, +13, +14, +15, +16, +17, +18, +19, or +20 mV; the peptides comprise at least 2 amino acids and no more than 11 amino acids; and the amino acid sequence of the peptides includes at least 2 L-Arginine residues, no more than 4 L-Arginine residues, and no other charged amino acids other than L-Arginine residues.

In some embodiments the carrier polymer is a highly carboxylated carbohydrate such as hyaluronic acid to which the peptide-bridging group B is linked via and amide bond to the carrier carboxyl groups. In order to achieve the required positive zeta potentials described herein for slowed vitreal diffusion such embodiment requires sufficient capping of the excess unlinked carboxyl groups to allow a net positive charge on the conjugated surface. This may be achieved by linking PEG(4-24)-amines, as amides, to 20% or 50% or >80% of the remaining free carboxyl groups, the attached PEG groups can also shield the conjugated anchoring peptides from degradative enzymes and from the immune system.

In some embodiments of the disclosed nanocarriers, the peptides are covalently attached to the nanocarriers via conjugation between hydroxyl groups on the surface of the nanocarriers and free carboxyl groups on the peptides (e.g., via an ester linkage). The peptides of the disclosed nanocarriers may have a formula: Z-AA0-AA1-AA2-AA3-AA4-AA5-AA6-AA7-AA8-AA9-AA10-Y, wherein Z is dicarboxylic acid in half-amide bond with AA0 or AA1 (e.g., where Z is suberic acid, adipic acid, glutaric acid, or succinic acid in half-amide bond with AA0 or AA1 and in direct ester linkage to a hydroxyl group on the surface of the nanocarriers); AA0 is present or absent, and when present, AA0 is selected from the group consisting of L-arginine, a naturally occurring amino acid with an uncharged side chain (e.g., sarcosine and glycine), and beta-alanine; AA1, AA2, AA3, AA4, AA5, AA6, AA7, AA8, AA9, and AA10 are present or absent, and when present are individually selected from L-arginine or a naturally occurring amino acid with an uncharged side chain; Y is an amide, a mono-substituted or di-substituted alkyl amide (e.g., methylamide, ethylamide, and dimethylamide), or a PEG(4-12) amide; with the proviso that: the peptides have a net positive charge and zeta potential between about +2 to about +9, +10, +11, +12, +13, +14, +15, +16, +17, +18, +19, or +20 mV; the peptides comprise at least 2 amino acids and no more than 11 amino acids; and the amino acid sequence of the peptides includes at least 2 L-Arginine residues, no more than 4 L-Arginine residues, and no other charged amino acids other than L-Arginine residues.

In some embodiments, the nanocarriers may be conjugated to peptides having a formula: X-peptide-Y, wherein: X is amino-PEG(4-12)-CO-, and Y is a mono-substituted or di-substituted alkyl amide (e.g., methylamide, ethylamide, and dimethylamide), or Y is a PEG(4-12) amide. Exemplary peptides may include, but are not limited to: $NH_2$-PEG(4-12)-CO-Val-Ile-Thr-Arg-Ile-Arg-$NH_2$ (SEQ ID NO: 7); $NH_2$-PEG(4-12)-CO-Leu-Tyr-Arg-Val-Arg-$NH_2$ (SEQ ID NO:8); and $NH_2$-PEG(4-12)-CO-Arg-Arg-Ser-Ser-Arg-Arg-$NH_2$ (SEQ ID NO:9) and the N-terminal amino group is covalently linked to a hydroxyl on the surface of the nanocarriers through a carbamate linkage.

In some embodiments, the disclosed nanocarriers further may comprise a drug or pro-drug, for example conjugated to the nanocarriers or peptides and/or adsorbed to the nanocarriers and/or peptides. In other embodiments, the disclosed nanocarriers may comprise a drug or pro-drug, such as a lipophilic drug or pro-drug that is confined to in the lipophilic core of the nanocarriers. In even further embodiments, the disclosed nanocarriers may comprise an antibody or an antigen-binding fragment thereof (e.g. a therapeutic antibody such as an anti-VEGF-1 antibody), for example, conjugated to the nanocarriers or peptides and/or adsorbed to the nanocarriers and/or peptides. In even further embodiments, the disclosed nanocarriers may comprise nucleic acid adhered to the surface of the nanocarriers, optionally wherein the nucleic acid is RNA such as RNA used for RNA-interference therapy including siRNA. (See Thakur et al., "Strategies for ocular siRNA delivery: Potential and limitations of non-viral nanocarriers," J. Biol. Eng'g 2012 6:7; and Turchinovich et al., "Non-viral siRNA delivery into the mouse retina in vivo," BMC Ophthalmology 2010, 10:25, the content of which is incorporate herein by reference in its entirety). Suitable siRNA's may include, but are not limited to siRNA's that interfere with expression of vascular endothelial growth factor receptor-1 (VEGF-1) such as Sirna-027. When the nanocarriers comprise nucleic acids, the anchoring peptides may include additional arginine residues (e.g., 3-4 arginine residues rather than only 2 arginine residues) and/or the anchoring peptides may have a higher degree of loading in order to offset the negative charge of the nucleic acids (i.e., such that the net positive-charge of the nanocarriers is at least +2 mV).

The disclosed nanocarriers may be administered to a subject in need thereof, for example, in a method of treatment. As such, the disclosed nanocarriers may be formulated as pharmaceutical compositions.

In some embodiments, the disclosed nanocarriers and/or pharmaceutical compositions comprising the disclosed nanocarriers are administered via injection into a body cavity of a subject in need thereof. In some embodiments, the body cavity comprises a polyanions and has a net negative charge. The disclosed nanocarriers may have a net positive charge and may be immobilized in the body cavity having a net negative charge via ionic interactions. In some embodiments, the disclosed nanocarriers may be utilized in an ocular nanotherapy. Suitable body cavities for administering the disclosed nanocarriers may include the vitreous humor, for example, where the disclosed nanocarriers are administered to the vitreous humor of a subject in need thereof to treat an ocular disease or disorder (e.g., age-related macular degeneration, diabetic retinopathy, and/or glaucoma), or retinopathy of prematurity (ROP).

The disclosed nanocarriers and/or pharmaceutical compositions comprising the disclosed nanocarriers may be administered to a subject having a neovascular retinal disease, for example, where the nanocarriers comprise an anti-angiogenic agent. In some embodiments, the neovascular retinal disease is macular degeneration.

The nanocarriers may be formulated based on the intended therapeutic use of the nanocarriers. For example, the nanocarriers may have an average effective diameter that is less than about 0.2 microns (e.g., when the carriers are formulated for intravitreal administration). In some embodiments, the nanocarriers may have an average effective diameter that ranges from 0.1 microns to 20 microns (e.g., when the carriers are formulated for intraperitoneal administration). Preferably, for intraocular applications, the carriers are optically transparent or substantially optically transparent (e.g., when the carriers are used in preparing a prodrug for intravitreal administration). For example, a transparent or substantially transparent carriers may absorb and reflect less than about 10%, 9%, 8%, 7%, 6%, 5%, 4%, 3%, 2%, or 1% of incident light and/or may have a total transmittance of at least about 90%, 91%, 92%, 93%, 94%, 95%, 96%, 97%, 98%, or 99% of incident light.

In some embodiments, the disclosed nanocarriers may be formulated for delivering anti-angiogenic, VEGF neutralizing proteins (e.g., as marketed under the trade names Lucentis™, Avastin™, and Eylea™). Anti-angiogenic, VEGF neutralizing proteins are used to treat eye disease by direct injection into the vitreous humor, the proteins all bind and neutralize the endogenous angiogenic protein, VEGF. Small synthetic molecule drugs (e.g., anti-inflammatory, anti-glaucoma, anti-infectious) can also be delivered by this route if their release can be sustained.

ILLUSTRATIVE EMBODIMENTS

The following embodiments are illustrative and should not be interpreted to limit the scope of the claimed subject matter.

Embodiment 1

Nanocarriers that are biodegradable or that can be excreted and have a net positive surface charge and zeta potential between about +2 to about +20 mV (e.g., +2, +3, +4, +5, +6, +7, +8, +9, +10, +11, +12, +13, +14, +15, +16, +17, +18, +19, or +20), wherein the net positive surface charge is provided by peptides that are covalently attached to the surface of the nanocarriers.

Embodiment 2

The nanocarriers of embodiment 1, wherein the nanocarriers comprise a polymeric carbohydrate and are transparent, and preferably have a diameter that permits for filter sterilizing.

Embodiment 3

The nanocarriers of embodiment 1 or 2, wherein the nanocarriers comprise dextran which optionally is a condensed dextran hydrogel, chitosan, pullulan, or a dendrimer.

Embodiment 4

The nanocarriers of any of the foregoing embodiments, wherein the peptides comprise C-terminal amide groups.

Embodiment 5

The nanocarriers of any of the foregoing embodiments, wherein the peptides comprise at least 2 amino acids and no more than 11 amino acids.

Embodiment 6

The nanocarriers of any of the foregoing embodiments, wherein the amino acid sequence of the covalently attached peptides includes at least 2 L-Arginine residues, no more than 4 L-Arginine residues, and no other charged amino acids other than L-Arginine residues, and where the amount of covalently attached peptides produces a positive average zeta potential of the particles ranging from about +2 to about +20 mV.

Embodiment 7

The nanocarriers of any of the foregoing embodiments, wherein the amino acid sequence of the attached peptides comprises an amino acid sequence of a human protein that is secreted into the extracellular matrix or that is found in vitreous humor, blood, urine, or saliva, or has an amino acid sequence that is at least 80% identical with the corresponding sequence from the human protein that is secreted into the extracellular matrix or that is found in vitreous humor, blood, urine, or saliva.

Embodiment 8

The nanocarriers of any of the foregoing embodiments, wherein the peptides include at their N-terminus a neutral amino acid residue selected from the group consisting of sarcosine, or beta-alanine.

Embodiment 9

The nanocarriers of any of the foregoing embodiments, wherein the peptides are covalently attached to the nanocarriers via conjugation between hydroxyl groups on the surface of the nanocarriers and free amino groups on the peptides.

Embodiment 10

The nanocarriers of any of the foregoing embodiments, wherein the peptides are covalently attached to the surface of the nanocarriers via carbamate conjugation between hydroxyl groups on the surface of the nanocarriers and an amino group appended to the peptide N-terminus, wherein the amino group is selected from the group consisting of a free alpha amino group on the peptides, a free beta, gamma, delta or epsilon amino acyl group on the peptides, as in epsilon aminocaproic acid, an amino-PEG(4-12) acyl amide of the peptide N-terminus, or a pyrrolidyl-3-carboxylate amide or pyrrolidyl-3-amidosuccinyl amide of an amino-PEG(4-12) acyl amide of the peptide N-terminus.

Embodiment 11

The nanocarriers of any of the foregoing embodiments, wherein the peptides are covalently attached to the surface of the nanocarriers via amide conjugation between carboxyl groups on the surface of the nanocarriers and an amino group appended to the peptide N-terminus, wherein the amino group is selected from the group consisting of a free alpha amino group on the peptides, a free beta, gamma, delta or epsilon amino acyl group on the peptides, as in epsilon aminocaproic acid, an amino-PEG(4-12) acyl amide of the peptide N-terminus.

Embodiment 12

The nanocarriers of any of the foregoing embodiments, wherein the peptides have a formula: B-Z-AA0-(AA1)$_n$-Y, where n is an integer between 1 and 10 where no less than two AA and no more than 4 AA are L-arginine, and all other AA are neutral (not lysine or glutaric acid or aspartic acid), wherein: B is present or absent, and when B is present, B is selected from the group consisting of amino-n-butoxy, amino-ethoxyethyloxy, amino-piperidyl (3, or 4)-oxy, amino-pyrrolidinyl (3)-oxy, amino-benzyl (3, or 4)-oxy, aminoethylamido-valeric acid (4)-oxy, amino-cyclohexyl (3, or 4)-oxy, and amino-cyclopentyl (3)-oxy; Z is absent or present, and when Z is present, Z is a dicarboxylic acid, including suberic, adipic, glutaric, dimethylglutaric, succinic in amide bond to AA0 or AA1, where the OH group of an above amino alcohol, B is bonded as an ester to the free dicarboxylic acid group in half-amide linkage to or AA1; AA0 is present or absent, and when present, AA0 is selected from the group consisting of L-arginine, a naturally occurring amino acid with an uncharged side chain (e.g., sarcosine and glycine), and beta-alanine; AA1 is L-arginine or a naturally occurring amino acid with an uncharged side chain; Y is an amide, a mono-substituted or di-substituted alkyl amide (e.g., methylamide, ethylamide, and dimethylamide), or a PEG (4-12) amide; with the proviso that: the peptides have a net positive charge and their multiple linkage to carrier produces nanoparticles having zeta potential between about +2 to about +20 mV; when peptide comprises from about 10% to about 50% of the conjugate mass.

Embodiment 13

The nanocarriers of embodiment 12 or 13, wherein B is an amino-PEG-carboxylic acid having between 4 and 16 ethylene glycol units in amide bond to AA0 or AA1, and Z is absent.

Embodiment 14

The nanocarriers of embodiment 14 wherein the conjugated modified peptide is amino-PEG (4-12)-CO-Arg-Arg-Tyr-Arg-Leu-Y (SEQ ID NO:16), where Y is amide or ethylamide.

Embodiment 15

The nanocarriers of any of the foregoing embodiments, except embodiment 3, in which the carrier contains surface carboxyl groups, as in hyaluronic acid or a carboxy terminal dendrimer wherein the linking amino group is amide bonded to these carboxyl groups in sufficient yield to give zeta potential from about +2 mV to about +20 mV in which some carboxyl groups remain un-linked or where some of the carboxyl groups are capped as neutral amides.

Embodiment 16

The nanocarriers of any of the foregoing embodiments in which amino-PEG-OH or amino-PEG-OMe of molecular weight ranging from 200 to 2,000 grams/mole are additionally appended to carriers through carbamate or amide bonds while comprising from about 10% to about 50% of the conjugate mass.

Embodiment 17

The nanocarriers of any of the foregoing embodiments formulated by mixing with clinical grade viscous hyaluronic acid (Healon) for immobilization at sites of administration.

Embodiment 18

The nanocarriers of any of the foregoing embodiments, wherein Y is an amide, a mono-substituted or di-substituted alkyl amide (e.g., methylamide, ethylamide, and dimethylamide), or a PEG(4-12) amide or a 3-pyrrolidyl-3-carboxylate amide or pyrrolidyl-3-amidosuccinyl amide of an amino-PEG(4-12) acyl amide of the peptide N-terminus; with the proviso that: the peptides have a net positive charge and their multiple linkage to carrier produces nanoparticles having zeta potential between about +2 to about +20 mV; when peptide comprises from 10-50% of the conjugate mass; the peptides comprise at least 2 amino acids and no more than 11 amino acids; and the amino acid sequence of the peptides includes at least 2 L-Arginine residues, no more than 4 L-Arginine residues, and no other charged amino acids other than L-Arginine residues.

Embodiment 19

The nanocarriers of any of the foregoing embodiments, wherein Z is a dicarboxylic acid selected from the group consisting of adipic acid, glutaric acid, and succinic acid in half-amide bond with AA0 or AA1 and in direct ester linkage to a hydroxyl group on the surface of the nanocarriers.

Embodiment 20

The nanocarriers of any of the foregoing embodiments further comprising a pro-drug conjugated to the carrier.

Embodiment 21

The nanocarriers of any of the foregoing embodiments further comprising a lipophilic drug loaded in the core of the nanocarriers.

Embodiment 22

The nanocarriers of any of the foregoing embodiments further comprising antibodies or antigen binding fragments thereof (e.g., anti-VEGF-1 antibodies) conjugated to the peptides.

Embodiment 23

The nanocarriers of an of the foregoing embodiments further comprising nucleic acid adhered to the surface of the nanocarriers, optionally wherein the nucleic acid is RNA (e.g., siRNA such as siRNA that inhibits expression of VEGF-1).

Embodiment 24

The nanocarriers of any of the foregoing embodiments, wherein the amino acid sequence of the peptides comprises an amino acid sequence of a human protein that is secreted into the extracellular matrix or that is found in vitreous humor, blood, urine, or saliva.

Embodiment 25

The nanocarriers of any of the foregoing embodiments, wherein the carrier-bonded peptides have a formula: X-peptide-Y, wherein: (1) X is a di-carboxylic acid of 4-10 carbons in length in half-amide bond with the N-terminus of the peptide, (2) X is succinic acid, glutaric acid, or adipic acid in half-amide bond to sarcosine which is in turn amide bonded to the N-terminus of the peptide, (3) X is succinic acid, glutaric acid, adipic acid, or suberic acid directly amide bonded to the N-terminus of the peptide when the peptide has an N-terminal proline, or (4) X is a dicarboxylated PEG (1-6 ethylene glycol units) half amide bonded to the peptide N-terminus and half amide bonded to the exocyclic amino group of 3-aminopyrrolidine; and (1) Y is an amide, (2) Y is a mono-substituted or di-substituted alkyl amide (e.g., methylamide, ethylamide, and dimethylamide), or (3) Y is a PEG(4-12) amide.

Embodiment 26

The nanocarriers of any of the foregoing embodiments, wherein the peptides are selected from the group consisting of: $NH_2$-PEG(8-12)-CO-Val-Ile-Thr-Arg-Ile-Arg-$NH_2$ (SEQ ID NO:7); $NH_2$-PEG(8-12)-CO-Leu-Tyr-Arg-Val-Arg-$NH_2$(SEQ ID NO:8); $NH_2$-PEG(8-12)-CO-Arg-Arg-Ser-Ser-Arg-Arg-$NH_2$ (SEQ ID: 9); and the N-terminal amino group is covalently linked to a hydroxyl on the surface of the particles through an amide linkage or a carbamate linkage.

Embodiment 27

The nanocarriers of any of the foregoing claims, wherein the peptides are selected from the group consisting of: 3-pyrrolidine-CONH-PEG(8)-CO-Tyr-Arg-Val-Arg-Ser-$NH_2$ (SEQ ID NO:4); and 3-pyrrolidine-CONH-PEG(8)-CO-Arg-Arg-Tyr-Arg-Leu-$NH_2$ (SEQ NO ID NO:5).

Embodiment 28

The nanocarriers of embodiment 12, wherein the appended esterified dicarboxypeptide [B-Z-AA0-(AA1)n-Y] comprising from about 10% to about 50% of the total nanocarriers mass is pyrrolidinyl (3)-oxy-adipic-Sar-Tyr-Asn-Leu-Tyr-Arg-Val-Arg-Ser-amide (SEQ ID NO:6).

Embodiment 29

Nanocarriers comprising the properties of embodiment 13 and of embodiment 17 in which both an ester-linked bioactive peptide (eg: SEQ ID NO:6) and a 3Arg or 4Arg anchoring peptide (eg: SEQ ID NO:5 or SEQ ID NO:9) stably attached as carbamates are simultaneously conjugated to the same CDEX particle, where bioactive peptide and anchor peptide each contribute from about 20% to about 40% of the conjugate mass, to enable simultaneous prolonged intravitreal residence and continuous drug release.

Embodiment 30

A pharmaceutical composition comprising the nanocarriers of claim 1 and a suitable pharmaceutical carrier, which may include, but is not limited to mixtures of cationic nanocarriers with natural poly-anions such as hyaluronic acid or heparins to immobilize and enhance the safety of the nanocarriers.

Embodiments 31

A method comprising administering the nanocarriers of any of the foregoing embodiments of a pharmaceutical compositing comprising the nanocarriers of any of the foregoing embodiments to a subject in need thereof.

Embodiment 32

The method of embodiment 31, wherein the nanocarriers are administered via injection into a body cavity comprising polyanions.

Embodiment 33

The method of embodiment 31, wherein the subject has an eye disease and the cavity comprises the vitreous humor.

Embodiment 34

The method of any of embodiments 31-33, wherein the eye disease is a neovascular retinal disease.

Embodiment 35

The method of embodiment 32, wherein the neovascular retinal disease is macular degeneration.

Embodiment 36

The method of embodiment 33, wherein the eye disease or disorder is diabetic retinopathy.

Embodiment 36

The method of embodiment 31, wherein the body cavity is selected from the group consisting of the vitreous humor, the intraperitoneal cavity, and the intracranial cavity.

Embodiment 37

Modified peptides having a sequence selected from: 4-aminocyclohexyl-O-adipoyl-Sar-Tyr-Asn-Leu-Tyr-Arg-Val-Arg-Ser-$NH_2$ (SEQ ID NO:6); or 3-pyrrolidyl-O-adipoyl-Sar-Tyr-Asn-Leu-Tyr-Arg-Val-Arg-Ser-$NH_2$ (SEQ ID NO:6); or 4-aminocyclohexyl-O-adipoyl-NH-PEG(4,8)-CO-Arg-Arg-Tyr-Arg-Leu-amide (SEQ ID NO:5); or 3-pyrrolidyl-O-adipoyl-NH-PEG(4,8)-CO-Arg-Arg-Tyr-Arg-Leu-amide (SEQ ID NO:5) and their carbamate conjugates with condensed dextran70, having zeta potential from +2 to +20 mV where peptide comprises 10-60% of the total conjugate mass or a 3-pyrrolidyl-3-carboxylate amide or pyrrolidyl-3-amidosuccinyl amide of an amino-PEG(4-12) acyl amide of the peptide N-terminus.

EXAMPLES

The following Examples are illustrative and are not intended to limit the scope of the claimed subject matter.

Example 1—Overview of Nanocarrier Technology

Here, we disclose a new approach to the anchoring of carrier nanoparticles within certain body spaces for local, continuous drug delivery, with particular emphasis on prolonged availability of drugs injected into the vitreous humor of the eye. Previously, slow delivery in the eye has relied on slowly diffusing large particles in the viscous gel environment or both smaller and larger ones with positive charges to better adhere to highly negatively charged polymers found in the vitreous. These types of carrier can be toxic to sensitive eye components, and can be hard to control kinetically. Arginine has been shown to be a safer source of (+)charge but has not previously been attached as described here, where its loss is well-controlled. We rely on small carriers (<200 nm diameter) with positive charges on their surface, where this charge is derived from small arginine-containing peptides with natural human amino acid sequences. The (+)charge per peptide is low, but many of these on a carrier surface can give strong adherence to polyanions in the eye. Uniquely here, the peptides are attached to the carriers via bridges which break down spontaneously in a first order process with half-lives of 1-4 weeks under physiological temperature and pH. Thus, over time the surface charge is slowly lost until the carriers no longer adhere and then readily leave the eye. Drugs within or attached to the carriers will have their own release rate which can be tuned to closely match the carrier particle release. Our preferred carriers are small enough to be sterile-filtered when fully loaded with peptides and drug.

The details of this invention include: description of exemplary peptides and the human proteins from which they are derived, appended groups included for linkage, with description of how these are synthesized and their breakdown rate evaluated, and examples of carriers, their properties, and how the peptides are attached to them.

In order to provide a net positive charge, be non-immunogenic, and to avoid side-reactions the peptides to be linked to carriers as esters contain between 2 and 11 naturally occurring L-amino acids in their normal sequence in human proteins of which 2 or 3, or 4 are L-arginine (Arg, R) residues. None are lysine, or Glu, or Asp and free carboxyl termini are preferably capped as amides. The N-terminal carrier-linking amine may also be derived from amino-PEG (n)-COOH, where n is an integer from 4-12, bonded to the peptide at its amino terminus. Alternatively, the peptides may have appended at their N-terminus an amide bonded di-carboxylic acid of 4-8 carbons in length for ester formation to amino alcohols, B, from which amino groups can form bonds to carriers. The N-terminal amino acid may be an added sarcosine (Sar, N-methylglycine) or may be L-proline from the parent protein sequence when the peptide is N-terminally capped with a di-carboxylate is such as succinate or glutarate or adipate or suberate. The N-terminal amino acid may be any naturally occurring L-amino acid when the di-carboxylic acid is adipic acid or a longer chain half-amide.

Peptide Examples

A heptamer peptide of +2 net charge within P18 of the matrix protein, PEDF is: Ac-Leu-Tyr-Arg-Val-Arg-Ser-Ser-amide (SEQ ID NO:10). This has a net charge of +1 when the N-terminus is capped by a dicarboxylic acid, as in: adipoyl-Leu-Tyr-Arg-Val-Arg-Ser-Ser-amide (SEQ ID NO:10), which then increases to +2 in a half ester of a di-carboxylic acid such as adipic acid as in R-O-adipoyl-Leu-Tyr-Arg-Val-Arg-Ser-Ser-amide (SEQ ID NO:10) or in an amido ester which may be bridged stably to a carrier through an amide bond to an amino-alcohol ester as in: Carrier-CO-amido-butyloxyadipoyl-Leu-Tyr-Arg-Val-Arg-Ser-Ser-amide (SEQ ID NO:10). It may be delivered to carrier with an amino-PEG cap as in amino-PEG(n)-CO-Leu-Tyr-Arg-Val-Arg-Ser-Ser-amide (SEQ ID NO:10). The latter peptide has net charge pf +3, which then becomes +2 upon carbamate attachment to carrier OH groups. Succinic, glutaric, adipic and suberic acids can also be used as metastable ester bridged linkers when an N-methyl amino acid (e.g., Sarcosine, Sar) is appended to the peptide N-terminus, as in: Carrier-CO-amido-butyloxyadipoyl-Sar-Leu-Tyr-Arg-Val-Arg-Ser-Ser-amide (SEQ ID NO:23).

Another series of human peptide sequences are shown, derived from human thrombospondin-1 (TSP-1) where a normal human sequence therein is: Gly-Asp-Gly-Val-Ile-Thr-Arg-Ile-Arg-Leu. Within this sequence the smaller Ac-Gly-Val-Ile-Thr-Arg-Ile-Arg-amide (SEQ ID NO:1) has +2 charge, and can be linked via an extended amino-PEG linker, or as an adipic ester as in: amino-R-O-adipoyl-Gly-Val-Ile-Thr-Arg-Ile-Arg-amide (SEQ ID NO:1), with alternative links analogous to those described above for the PEDF series, as in: RO-adipoyl-Sar-Gly-Val-Ile-Thr-Arg-Ile-Arg-amide (SEQ ID NO:11). Amino-PEG-peptides comprising just the last 4-5 amino acids of the above sequence are also appropriate as +2 charge anchor peptides.

The same approach can be taken with sequence from human fibrinopeptide B-beta, which circulates in blood and is found in human urine, thus unlikely to be immunogenic. The peptide contains the sequence: Ser-Gly-Gly-Gly-Tyr-Arg-Ala-Arg-Pro-Ala (SEQ ID NO:12). Appropriate linkable derivatives as above, from the fibrinopeptide may include: R-O-adipoyl-Gly-Gly-Tyr-Arg-Ala-Arg-Pro-amide (SEQ ID NO:13); or R-O-adipoyl-Sar-Gly-Tyr-Arg-Ala-Arg-Pro-amide (SEQ ID NO:14). Amino-PEG-capped peptides comprising the truncated distal Tyr-Arg-Ala-Arg-Pro-amide (SEQ ID NO:24) from the above sequence are also appropriate as +2 charge anchor peptides.

For anchoring peptides with +3 charge that can be conjugated to dextran carriers, we select the natural sequence pentapeptide: Arg-Arg-Tyr-Arg-Leu (SEQ ID NO:5) from within the sequence: . . . Phe-His-Arg-Tyr-Arg-Leu-Pro . . . (SEQ ID NO:15) conserved in chaperone proteins Hsp20 and alpha-A crystallin (aa118-124), which are found in the circulation and in the eye [AR Clark et al. Crystal structure of R120G disease mutant . . . J Mol Biol 408:118 (2011)]. Thus amino-PEG (4-12)-CO-Arg-Tyr-Arg-Arg-Leu-amide (SEQ ID NO:5) will display net charge of +3 for every peptide appended to a carrier OH group through amino-terminal linkage.

Ester linkable peptides from all the human sequences described above have 6-7 amino acids in exact human sequence. However, as many as 10 in sequence are acceptable, with up to one additional linker amino acid at the N-terminus and/or a single di-carboxylic acid appended at the N-terminus.

Other positively charged small peptides found in urine include fragments of human protamine, which is very rich in Arg residues, thus can enhance (+)charge, even in small peptides. One such naturally occurring protamine fragment is Pro-Arg-Arg-Arg-Arg-Ser-Ser-Ser-Arg-Pro (SEQ ID NO:16). Based on this sequence, smaller portions therein can be used as in: R-O-adipoyl-Arg-Arg-Ser-Ser-Ser-Arg-Pro-amide (SEQ ID NO:17), or a 4Arg version as in R-O-adipoyl-Pro-Arg-Arg-Arg-Arg-Ser-amide (SEQ.ID18). Each of the above examples provides +3 net charge on the ester-linked peptide. Also, with proline at the N-terminus adipate, glutarate and succinate are also acceptable linking moieties to the carrier. Thus, amino-PEG(4-12)-CO-Pro-Arg-Arg-Arg-Arg-Ser-amide (SEQ ID NO:18) is an appropriate +4 peptide to be linked, and may also be embodied in N-terminal bridged ize with displacement of the ester, as in: amino-R-O-glutaryl-Pro-Arg-Arg-Arg-Arg-Ser-Ser-amide (SEQ ID NO:18), also giving a +4 net charge, where Pro is from the normal sequence, are contemplated herein, and is less likely than primary amino acid to cyclize through attack on the ester bridge.

The carriers described here include (but are not limited to) dendrimers and polymeric carbohydrate gels. OH-terminal carriers gain the total charge of carbamate appended amino-acyl or amino-PEG peptides, while excess peptides are needed for COOH-terminal carriers to maintain cationic charge. Peptides, each having +4 charge when linked as amides to just 30% of a 64 carboxyl dendrimer, will add +76 charge per dendrimer, with only 45 COOH then remaining, these have +31 net charge. With 40% of the available sites linked this way, the net charge will be +64, thus will be more tightly anchored via multiple weak forces to vitreal hyaluronic acid.

Synthesis of the ester-bridged versions can be achieved by attaching a short N-BOC-amino-alcohol (e.g., 4-BOC-amino-1-butanol or 4-N-BOC-amino-cyclohexanol, or N-BOC-3-pyrrolidinol) in ester linkage with the free carboxyl group of adipic acid, after reaction with adipoyl chloride. The BOC-amido-alkyl half-ester of adipic acid is then N-terminally added to the peptide by well-established solid state amide coupling techniques to an appropriate solid state peptide at its free sarcosine N-terminus, after which standard acidic de-blocking and peptide release then gives the salt of amino-alkyloxy-ester-Sar-AA1-AA2-AAn . . . -amide (where n=1-10) with an amide capped C-terminus, ideally to maintain positive charge, and where 1, 2, 3 or 4 of the aa residues are Arginine, flanked and connected to each other by normal human sequence identical to that found in their parent protein. The free N-terminal amine group is then amide bonded to a carrier (e.g., a carboxy dendrimer, hyaluronic acid, and the like) by common methods of acyl activation, so that multiple amido ester-linked (+ or ++ charged) peptides are present on the carrier surface. Typically for a water-soluble carrier, coupling will utilize water soluble carbodiimide and sulfo-NHS. Activated but unreacted carboxyl groups of the carrier can then be capped and neutralized with other uncharged amides (e.g. by reaction with methoxy-PEG-amine, beta-alanine amide, etc.) to increase overall positive charge (positive zeta potential). For carbamate linkage to an OH terminal carrier, the OH groups are first activated by reaction in DMSO, with either carbonyldiimidazole (CDI) or with p-nitrophenylchloroformate (pNP-Cl). The activated carriers are then linked to peptide by reaction of free non-alpha amino groups of amino-alkyl-peptide, amino-PEG-peptide or amino-alkoxy ester peptides. Any remaining activating groups are then discharged by reaction with excess ethanolamine or PEG (4-12)-amine. A pNP-Cl advantage is colorimetric estimation of appended activating groups, and detection of complete removal.

Amino Alcohols for Ester Coupling

Our use of several varied amino-alkoxy esters gives a range of spontaneous hydrolytic rates of ester breakdown at physiological temperature and pH which can be predicted from kinetic analysis of model esters. Inclusion of an ester bridge insures gradual loss of the anchoring charge, and can be adjusted to control the duration of intravitreal residence through continuous decline in zeta potential with time.

An important aspect of the peptide-loaded carriers is that they have a positive zeta-potential, i.e. a net positive charge concentrated on their surface in order to immobilize them at their site of injection through multiple weak ionic interactions with polymeric anionic groups in the vitreous or on mucosal surfaces. This derives from the fact that each attached peptide, when esterified has a net charge of at least +1, and is especially critical for use in the eye, which contains high concentrations of the viscous poly-anionic hyaluronic acid (HA). Thus an ideal particle to be used for intravitreal injection will be less than 200 nm in diameter when fully charged with peptide and drug, a size that does not impede diffusion out of the eye when neutral or negatively charged, but in our system will have net charge of +40 to +240 per 100-150 kDa particle, for long-term anchoring. Ideally, >50% of particles injected in 0.05 ml should be contained within a 0.25-0.50 ml spherical volume at the injection site, if measured 7 days post-injection, because of adherence to HA in the vitreous humor. This can be established by light loading (1-3%) with rhodamine, cyanine7 or other fluorophores, attached to the peptide-loaded carriers, then injected (1-50 ul) into rabbit vitreous or rodent eyes, as in FIGS. 8 and 9.

Measuring Peptide Release Half-Life.

Figure 8:
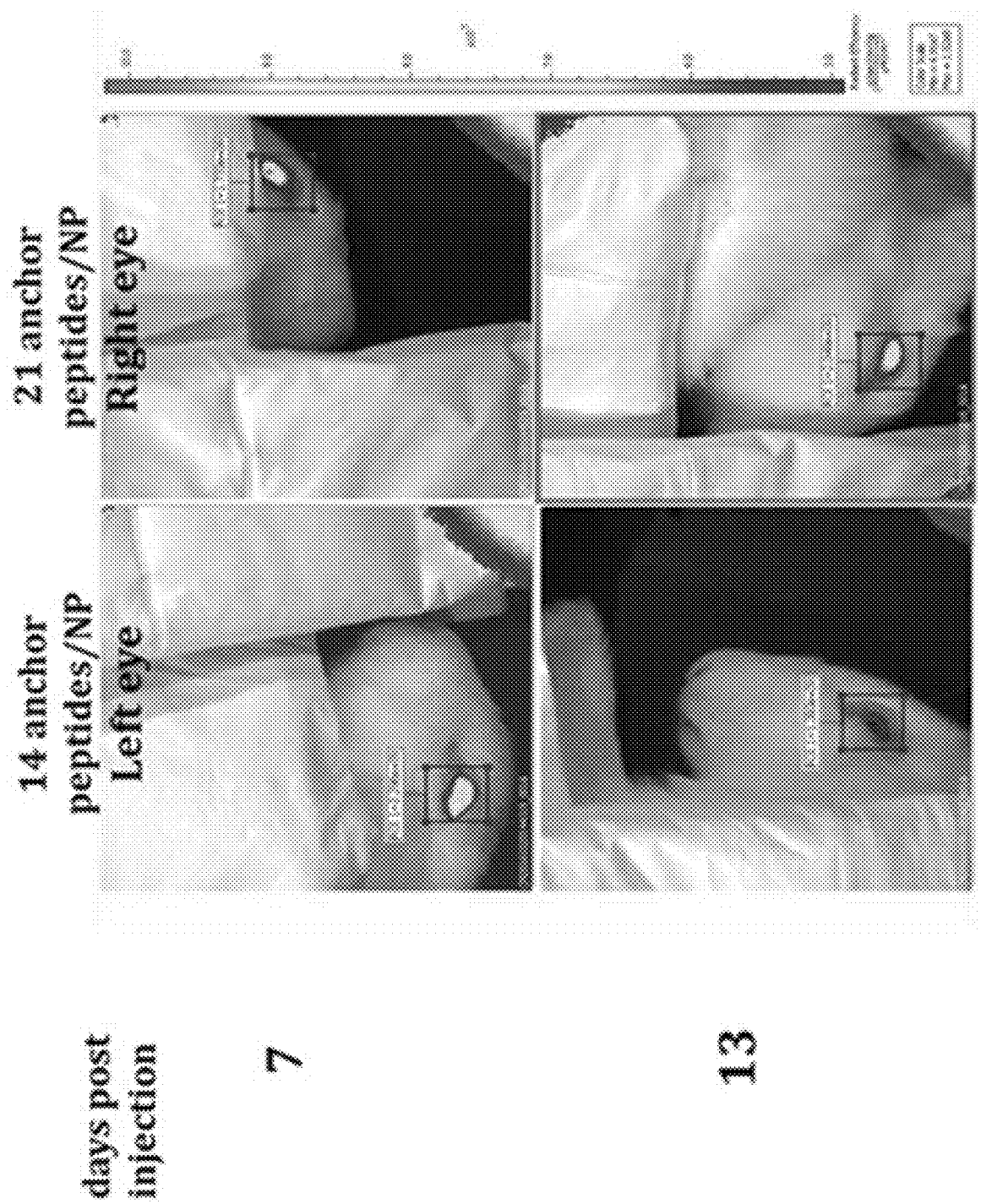
FIG. 8. Slowed rabbit eye clearance in vivo with Cy7-tagged 3R-peptide CDEX conjugate. 20 μl of anchor peptide amino-PEG8-RRYRL-amide (SEQ ID NO:5) conjugate to CDEX (2.5 mg/ml) along with conjugated 0.05 moles/particle Cy7-amine was injected into rabbit eyes on day one. Left eye 14 peptides/particle, right eye 21 peptides/particle. Increased peptide load in right eye allows longer residence of conjugate in eye, while left eye has lost >90% of fluorescence.
Figure 9:
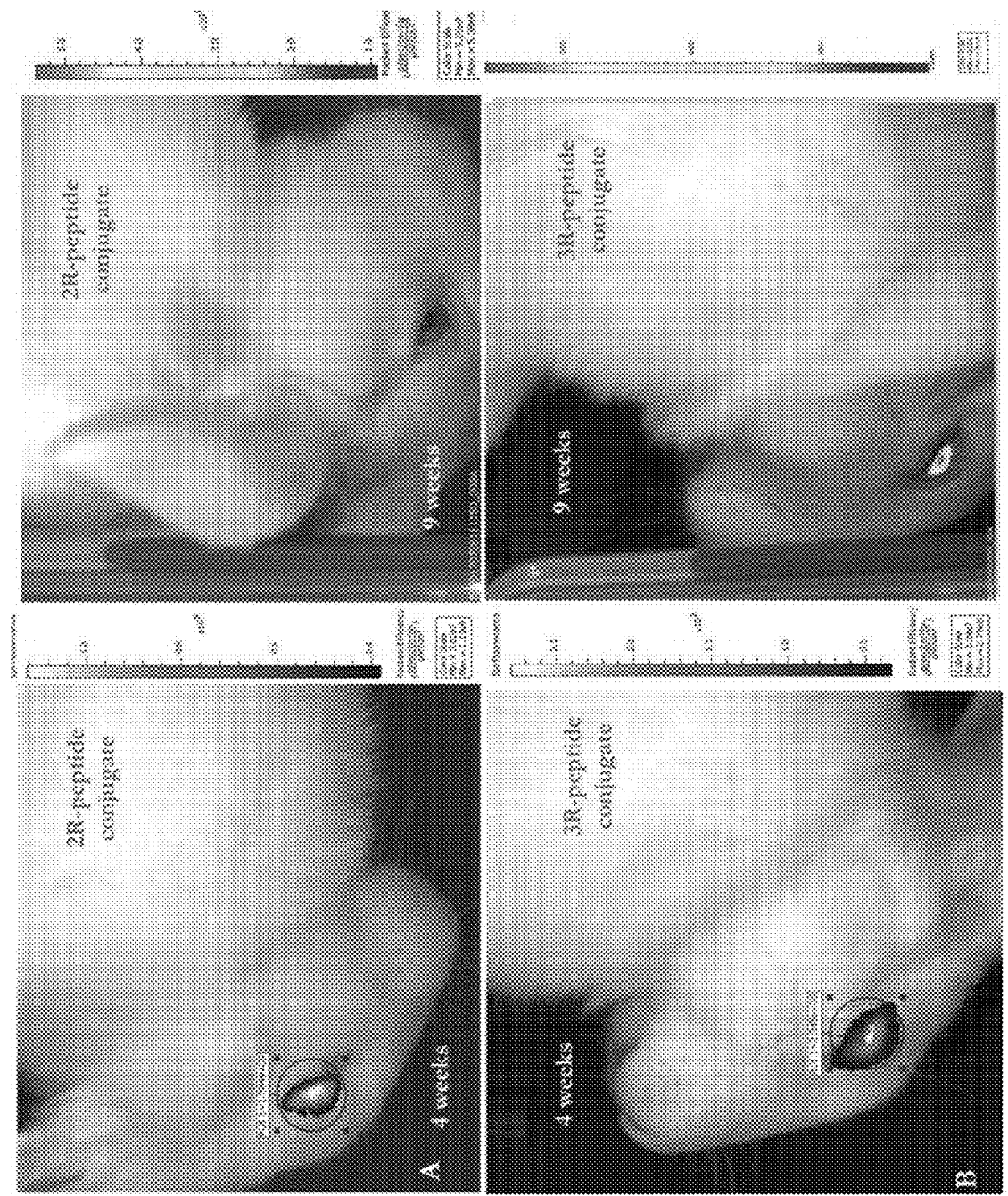
FIG. 9. Rabbit eye imaging by IVIS. Measurement of number of photons per area (excitation: 745 nm; emission: 800 nm). A: Left: IVIS scan after 4 weeks experiment. Right: IVIS scan after 9 weeks experiment. B: Left: IVIS scan after 4 weeks experiment. Right: IVIS scan after 9 weeks experiment. 3R peptide conjugate (SEQ ID NO:5) is seen to be retained longer in the eye compared with 2R peptide (SEQ ID NO:4) conjugate at similar peptide loading.

For use in the eye, the ideal half-life of ester cleavage by simple hydrolysis at 37° C. and pH 7.4 should be 20-60 days. Approximately 0.1-1 mg of peptide attached to 0.1-1 mg of the carrier would be delivered in the eye in a maximum 50₁11 injection volume. Our carriers will not pass through a 30 kDa MWCO centrifugal spin filter. Thus BCA protein analysis of increasing peptide, with time in filtrate after 30 kDa filtration of a loaded carrier sample in buffer estimates the half-life for peptide release in buffer. For confirmation in actual vitreous humor (e.g., rabbit) at time points post injection LC-MS estimation of the peptide in vitreous extract follows precipitation of excess HA after adding 3 volumes of ethanol. The half-life of residence of peptide-conjugated carriers in the vitreous of test animals such as rabbits was measured by tagging the carriers with long wavelength dyes (eg; Cyanine7) and measuring residual eye fluorescence over time by in vivo imaging system (IVIS), with excitation at 745 nm, emission 800 nm (FIGS. 8 and 9). Free intravitreal peptide is assayed after centrifugation via 30 kDa MWCO spin filter.

Drugs and Pro-Drugs for Delivery.

Hydrophobic small molecule drugs may be contained within hydrophobic cores of condensed gel particles (e.g., cholesteryl hyaluronic acid or cholesteryl dextran) or may be attached through labile (e.g., ester) bonds to unreacted surface groups. Antibody attachment (e.g., Avastin) will be through a bi-functional linker, containing an ester bridge, for example (amino-alkoxy ester-peptide-maleimide), where the proximal end is-bonded to the carrier and the distal maleimide is bonded to a cysteine sulfhydryl group obtained by TCEP or DTT reduction of one or more antibody disulfide groups or to VEGF-binding proteins that have been genetically modified to include a single free cysteine residue. Ester hydrolysis then releases the attached protein drug.

Example 2—Generation of Dextran Nano-Gels 4 g of dextran (M.W. 70,000, unit M.W. 190) was dried by co-evaporation with anhydrous pyridine in vacuo and activated by reaction with 93 mg 1,1'-carbonyldiimidazole (CDI) in 100 mL of anhydrous dimethyl sulfoxide (DMSO) at 25° C. under stirring for 4 h. Cholesteryl-amine was synthesized by modification of cholesteryl chloroformate with a 3-fold excess of 2,2'-(ethylenedioxy) bis (ethylamine) and purified by column chromatography on silicagel using a stepwise gradient of methanol in dichloromethane. 342 mg of cholesteryl-amine dissolved in 10 mL of DMSO was added to the activated dextran, and reaction mixture was stirred for 24 h at 25° C. The product (CDEX) was purified by dialysis in semi-permeable membrane tubes (MWCO 12-14,000) against water at 4° C. under stirring overnight, sonicated for 15 min and, then, freeze-dried. Total yield was 86%.

| Micro/nanogel | Particle size, nm | PDI | SD | Yield, % | Treatment |
|---|---|---|---|---|---|
| CDEX | 55 (100%) | 0.27 | 4 | 86 | Sonication |

Example—3 Activation of Nano-Gels

Nano-gel particles can be modified before charging with amino-peptides or peptide intermediates using chemical activation of hydroxyl groups on dextran/dextrin with 1,1'-carbonyldiimidazole. 210 mg CDEX was dried by co-evaporation with anhydrous pyridine and mixed with 36 mg 1,1'-carbonyldiimidazole (CDI) in 10 mL anhydrous DMSO. Reaction mixture was stirred for 4 h at 40° C. The activated CDEX was purified by dialysis in semi-permeable membrane tubes (MWCO 12-14,000) against water at 4° C. under stirring overnight and, then, lyophilized. Total yield of the imidazole-activated CDEX was 69%. Proton NMR showed that 58 imidazole groups was attached to the polymer molecule (0.7 mmol imidazole moieties per 1 g).

45 nEq of the complex CDEX were dissolved in a solution of DMSO:pyridine 1:1 (v:v) then, 63 µEq of pNP-Cl were added to the solution and 3 mM of DMAP. The reaction was incubated at −40° C. overnight. An aliquot was taken from the reaction and mixed with ethyl acetate. After centrifugation (14,000 g, 1 minute, room temperature), the pellet was dissolved in D2O and proton NMR showed the presence of the CDEX-pNP. After weighing and dilution into a specified volume of NaOH (0.1 M), the sample was evaluated by UV (λ=400 nm, pH:8 Cε: 18.234 M-1 cm-1) for total pNP content. UV spectrophotometry showed 108 pNP per particle of CDEX.

Example 4—Conjugation of Amino-PEG-Peptides

Amino-PEG(12)-peptides containing 1, 3 or 4 arginine residues (AP1, M.W. 1,200; AP3, M.W. 1,375, and AP4, M.W. 1,550) have been conjugated with CDI-activated CDEX nanogel and investigated in biological systems. Urethane bonds (carbamates) formed in this reaction are stable in most biological environments.

Imidazole-activated CDEX (20 mg) was dissolved in 0.5 mL water, and pH was adjusted to 8 with sodium bicarbonate solution. 9.6 mg of a 3-Arg peptide AP3, amino-PEG(12)-CO-Arg-Arg-Ser-Arg-amide (SEQ ID NO:19), was dissolved in 0.2 mL DMF and mixed with the CDEX solution. Reaction was continued overnight at 25° C. and, then, quenched with 5 µL ethanolamine overnight at 4° C. Carrier-peptide conjugates were purified by dialysis in semi-permeable membrane tubes (MWCO 12-14,000) against water at 4° C. under stirring overnight and, then, freeze-dried. The reaction was repeated similarly for 9.6 mg AP3, and 10.9 mg AP4.

Carbamate Linkage of Amino-PEG Peptide with 3 Arg Residues

| Sample | Peptide, % | Size, nm (SD) | PDI | Z-potential, mV | Yield, % |
|---|---|---|---|---|---|
| CDEX-AP3 | 31 | 124 ± 1.4 | 0.167 | 4.58 | 58 |

Alternative Carbamate Attachment of Arg-Peptide with Long Wavelength Dye

An especially favored small 3-Arginine peptide is RRYRL (SEQ ID NO:5), because this sequence occurs naturally in two eye proteins, alpha A crystallin and Hsp20. Its conjugate to CDEX can be followed by an In Vivo Imaging System (IVIS) if the conjugate is tagged with cyanine amine dye. A UV-VIS spectrum of the 3Arg peptide (SEQ ID NO:5) and the Cy7 dye conjugated to the nanocarrier (Cy7-CDEX70-3pyrrol-PEGS-RRYRL-NH2) was prepared. The $\lambda_{max}$ tyrosine of the peptide was 275 nm with an estimated 67 peptides per particle of CDEX. The $\lambda_{max}$ of Cy7 was 750 nm with an estimated 0.5 dye molecules per particle of CDEX.

CDEX Conjugation with Amino-PEG(4)-Arg-Arg-Tyr-Arg-Leu-Amide (SEQ ID NO:5).

5 mg (0.067 µmoles containing 25 µmoles free glycosyl units) of the cholesterol-dextran complex (CDEX) synthesized from dextran-70 kD was dissolved in 200 µl of anhydrous DMSO. Then 10 µl of dry pyridine was added to the solution, followed by 1.8 mg (8.67 µmoles) of 4-nitrophenyl chloroformate.

After 5 minutes, 4 µl of 4-(dimethylamino)pyridine (DMAP) stock solution at 150 µM in DMSO was added to achieve a final concentration of 3 mM. The reaction was incubated 1 hour at room temperature, after which was added 240 µg (0.33 µEq) of Cyanine7 amine (Cy7), stock solution at 20 mM in DMSO. The reaction was incubated during 1 hour at 50° C. Then, 29.2 mg (26 µmoles) of the amino-PEG-peptide (TFA salt) was pre-dissolved in 100 µl of anhydrous DMSO with 3 µl (34.7 µEq) of triethylamine (TEA). This solution is added to the reaction. The mixture (approx. 300 µl) was reacted in a 2 ml sealed vial at 50° C. for 72 h. After cooling to room temperature 26 µmoles of m-PEG$_4$-NH$_2$ was added to quench the reaction, for 1 hour at 37° C. The solution at RT was mixed with 1.0 ml of 0.1M hydrochloric acid. It was then dialyzed twice against 2 liters of 0.001 M HCl over 2 days at room temperature, using 12000 MWCO dialysis tubing. The dialyzed solution was sterile-filtered (0.2 µm), frozen and lyophilized.

The conjugated powder was dissolved in water at 0.2-2 mg/ml UV (λ=275 nm) and VIS (λ=750 nm) spectrum obtained. Covalent peptide linkage was estimated by UV spectrum, using a molar extinction coefficient of 1,100 per peptide tyrosine residue at 275 nm after correction by subtracting the UV spectrum of the same concentration of unreacted CDEX. The amount of Cy7 linked to the CDEX was established by Cy7 molar extinction of 199,000 of dye at 750 nm. A sterile-filtered solution of CDEX conjugate having 21 peptides per CDEX monomer and 0.05 Cy7 per CDEX monomer was then tested in comparison to conjugate having only 14 peptides/CDEX, and similarly tagged with Cy 7 dye. (See FIG. 7.)

CDEX Conjugation with 3-pyrrol-O-adipic-N-Sar-Tyr-Asn-Leu-Tyr-Arg-Val-Arg-Ser-amide (SEQ ID NO:6).

Synthesis of 6-{[1-(tert-butoxycarbonyl)pyrrolidin-3-yl]oxy}-6-oxohexanoic Acid.

3 mEq of adipic chloride were dissolved in 10 ml of dichloromethane (DCM) at room temperature under stirring. On the other hand, 1 mEq of the amino-alcoxy compound was dissolved in DCM with 1 mEq of triethylamine (TEA). This solution was added to the first one dropwise. After 30 minutes of reaction, the mixture was dried under vacuum and the crude was dissolved in a solution of sodium bicarbonate 1 M. The solution was washed with ethyl acetate and both phases were mixed in a separation funnel. The aqueous phase was extracted and the pH was adjusted to 3-4 with 1M HCl. Then, the solution was extracted with ether. The organic phase was dried under vacuum. Appearance: yellow-orange oil. The molecular weight of the compound was 315.36 g/mol. The yield of the reaction was 46.6%. $^1$H NMR (500 MHz, Chloroform-d) δ 4.96 (p, J=7.1 Hz, 1H), 4.10 (dd, J=9.5, 7.0 Hz, 1H), 3.78 (dt, J=9.5, 7.1 Hz, 1H), 3.52 (dt, J=9.5, 7.1 Hz, 1H), 3.37 (dd, J=9.4, 7.1 Hz, 1H), 2.63 (td, J=12.5, 1.5 Hz, 1H), 2.40-2.30 (m, 2H), 2.32-2.22 (m, 3H), 2.08-1.77 (m, 3H), 1.66-1.55 (m, 1H), 1.47 (s, 9H).

Synthesis of the Ester Prodrug 3-pyrrol-O-adipic-N-Sar-Tyr-Asn-Leu-Tyr-Arg-Val-Arg-Ser-amide (SEQ ID NO:5).

To HN-Sar-YNLYRVRS (SEQ ID NO:5) on Rink Amide 4-Methylbenzhydrylamine (MBHA) resin in DMF was added 1.5 mEq of Comp 1, 1.45 mEq (1-[Bwas(dimethylamino)methylene]-1H-1,2,3-triazolo[4,5-b]pyridinium 3-oxid hexafluorophosphate) (HATU), and 6 mEq of N,N-diisopropylethylamine (DIPEA). The reaction mixture was shaken on a mechanical shaker overnight (16 h) at room temperature. The resulting peptide was cleaved from the resin using a mixture of 95% trifluoroacetic acid (TFA), 2.5% water, and 2.5% triisopropylsilane for 3 h. Crude peptide was precipitated from this solution using cold diethyl ether before purification by HPLC. Appearance: white powder. The molecular weight of the compound was 1337.55 g/mol. The yield of the reaction was 26%. A mass spectrum analysis of the peptide was performed which exhibited a peak at 1336.8091 (m/z).

CDEX Conjugation with 3-pyrrol-O-adipic-N-Sar-Tyr-Asn-Leu-Tyr-Arg-Val-Arg-Ser-amide (SEQ ID NO:6).

After the CDEX activation, the sample (mass: 2.3 mg) was dissolved in EtOAc and was centrifuged (14,000 g, 1 minute, room temperature). The pellet was dissolved in DMSO (300 µl) and the mixture was rotary-evaporated to remove trace solvent. Then, 6.75 µEq of the prodrug were dissolved with 16.9 µEq of TEA (proportion 1:2.5) in anhydrous DMSO (200 µl). This mixture was added to the first one and the vial was sealed under anhydrous conditions in a nitrogen atmosphere. The reaction was placed in an orbital shaker at 100 rpm, 45° C. over 3 days.

After 3 days, the reaction was stopped. To quench the active pNP, 13.5 µEq of m-dPEG®$_4$-amine were added to the reaction and it reacts during 1 hour at room temperature. After that, 0.01 M of HCl solution was added dropwise getting the final pH=4. The mixture was dialyzed against 2 liters of HCl 0.1 mM at 4° C. during 24 hours changing the bath every 4 hours. MWCO: 50,000 Da. The solution was sterile-filtered and freeze-dried. Results have showed in Table 1.

TABLE 1

Characterization of CDEX70-3pyrrol-adipic-N-Sar-Tyr-Asn-Leu-Tyr-Arg-Val-Arg-Ser-amide (SEQ ID NO: 5).

| | |
|---|---|
| Yield (%) | 78 |
| Size (nm) | 178.3 ± 9.42 |
| Zeta potential (mV) | 2.31 ± 0.38 |
| Peptide/CDEX by BCA | 30 |
| Peptide/CDEX by UV | 57* |
| Half-life (physiol. cond.) (days). | 28 |

*The peptide quantification was taken to be that established by UV Tyr spectrum. UV (based on Tyr molar extinction of 1,100 at 276 nm). BCA is considered less accurate when peptide is appended to carrier, where free peptide is used as BCA reference standard.

Example 5—Characterization of CDEX-Peptide Conjugates

Peptide content in carrier-peptide conjugates was measured using a Pierce BCA Protein Assay based on the calibration curve obtained with the corresponding free peptide. Peptide analysis was performed as follows: 20 mg/mL stock solution of peptide in water was used to prepare serial ½ dilutions of standards. Then, BCA working reagent (WR) was prepared by mixing 50 mL of BCA reagent A (50 mL) with 1 mL of BCA reagent B. 25 of each standard dilution and a carrier-peptide conjugate sample (3-5 mg/mL) were placed into 96-well plate in triplicates, then 200 µL of WR was added to each well, and the plate was mixed thoroughly in shaker for 30 sec. Plate was covered and incubate at 37° C. for 30 min, cooled at 25° C., and the absorbance was measured at 562 nm using a plate reader. Peptide content (%) in the samples was calculated based on the calibration curve of free peptide.

Sample characteristics (particle size, polydispersity and zeta-potential) were measured by a dynamic light scattering method using Malvern Zeta Sizer Nano-S90 instrument according to the manufacturer recommendations. Briefly, hydrodynamic diameter (dh) and polydispersity index (PDI) of nanogel/microgels were obtained for 1 mg/mL aqueous solutions at 25° C. in triplicates after sonication for 30 min and centrifugation at 12,000 rpm. Zeta-potential of the samples was measured for the same solutions in standard 1 cm-cuvettes using zeta-potential option in the company's software. Average of five measurements±SD was registered.

Example 6—L-Arginine Peptide-Conjugated Nanocarriers for Sustained Intravitreal Drug Release Reference is made to the article by Li et al., "Sustaining Intravitreal Residence With L-Arginine Peptide-Conjugated Nanocarriers," Invest. Ophthalmol. Vis. Sci. 2017; 58:5142-5150, October 2017, the content of which is incorporated herein by reference in its entirety.

Abstract

Neovascular retinal diseases affect millions of people worldwide, and result in loss of vision and blindness if left untreated. Intravitreal injection of angiogenic antagonist proteins is currently the standard and most efficient method for retinal drug delivery. However, repeated injections are required to maintain effective drug concentrations, imposing treatment burdens, pain and risk of complications on patients. Sustained release of therapeutics by injecting colloidal carriers is a promising approach to reduce injection frequency. However, the micron scale of carriers' dimensions required for slow diffusion can potentially promote glaucoma and inflammation. Small, poly-cationic particles can be immobilized in vitreous through multiple ionic interactions with hyaluronic acid, resulting in slow diffusion, but such particles are generally toxic. Recently, particles containing L-Arginine as the only cationic source in their polymeric structure have been reported with greatly improved biocompatibility. Here, we synthesized and examined a novel type of biocompatible dextran-based nano carrier (<50 nm in diameter) conjugated stably with peptides containing L-Arginine for sustained release of therapeutic agents in the vitreous. We experimentally confirmed the poly-anion binding by competition studies with protamine in isolated rodent vitreous. We found that the diffusion rate of nano-carriers was inversely related to the values of zeta potential ex vivo in freshly isolated rat vitreous and observed increased intra-ocular half-lives in vivo. The longest clearance period in vivo was over 240 days.-Histological examination demonstrated no adverse effects on ocular morphology and organization at 3 weeks to 36 weeks. By combining the advantages of a small size and a long half-life, our novel peptide-conjugated carriers provide a safe and clinically practical means of sustained therapeutic release of agents against posterior eye diseases.

Introduction

Retinal and posterior segment diseases affect nearly 10 million people in the United States [1]. Untreated, they result in loss of vision. The effective treatments largely rely on a safe intravitreal (IVT) drug delivery. The unique anatomical and physiological barriers of the eye block outside drug molecules from entering the posterior segment, thus, leaving the delivery efficiencies of conventional topical or systemic/oral drug administrations to be less than 5%. Currently, intravitreal injection is the most efficient method for posterior eye drug delivery. This directly delivers active agents near the lesions, increasing the local drug concentration with low systemic exposure. Intravitreal injection is the primary method to treat endophthalmitis, sub-macular/vitreous hemorrhage, retinal vascular occlusion, advanced exudative age-related macular degeneration (AMD) and diabetic retinopathy. Acceptance of intravitreal injections has grown rapidly because of the injection of vascular endothelial growth factor (VEGF) inhibitors, which slow down the progress of neovascular retinal diseases, such as AMD and diabetic retinopathy. In 2012, more than 2.3 million injections were reported, and the number is estimated to be nearly 6 million in 2016. Patients will endure a burden of frequent injections over the long-lasting treatment period. Most therapeutic agents are typically eliminated from vitreous in a short time following their administration. Consequently, repeated injections are needed to maintain a therapeutically effective concentration in the posterior eye. For example, the half-life of Ranibizumab (a VEGF inhibitor for treatment of advanced AMD) in human vitreous is approximately 9 days, requiring one administration per month. Frequent intravitreal injections raise the patients' discomfort, and cumulatively increases the risk of potential complications, such as vitreous hemorrhage, cataract and endophthalmitis [1,2]. Additionally, frequent outpatient visit is a burden on patients, who typically cannot drive, and significantly increase total treatment costs.

In recent years, there have been efforts to overcome the shortcomings of multiple injections by extending the time of therapeutic release after delivery. Use of the slow-released colloidal drug carrier is typical. The latter are normally nano/micro-spheres made of biodegradable materials, with drug molecules embedded in their body or coated on their surface. After injection, the carriers remain in the vitreous over a relatively long time and slowly release the therapeutic molecules during their breakdown to smaller fragments to enable complete clearance. One critical limitation of colloidal carriers is their relatively large size. Colloidal carriers generally rely on large particle size (over 1 µm) to slow the diffusion through the viscous vitreous. Large colloidal carriers are not amenable to sterile filtration, and they or their breakdown products with a continuum of intermediate sizes may block vision and/or may block or interact with the trabecular drainage. 200-nm polystyrene particles coated with cationic amine groups showed diffusion rates of 1000-fold slower than their neutral or anionic counterparts in bovine vitreous [3]. Use of such cationic carriers, however, was not clinically practical since the particles are conjugated with multiple amino groups, which, along with most other cationic groups, are toxic, especially when the particles are of a size that can be engulfed by cells.

Recently, it has been reported that when the positive charge is entirely derived from L-Arginine (L-Arg), small cationic particles could be at least two orders of magnitude less toxic to cells. Zern et al [4] described a systematic comparison of cytotoxicity among cationic nanoparticles with varied sources of positive charges, including L-Arg and D-Arg. While all the particles are capable of forming complexes with polyanions, the L-Arg-based carriers were at least 200-fold less toxic than the non-arginine based cationic carriers and at least 10-fold less toxic than D-Arg carriers. L-Arg could be a practical and safe cationic group for clinically applicable nanoparticle carriers in vitreous humor.

Thus, we designed and fabricated a novel type of L-Arg based cationic nanoparticles, aiming to establish non-toxic, biocompatible therapeutic carriers for ocular drug delivery. Our nanoparticles were less than 50 nm in diameter, made from the neutral polysaccharide, dextran, with L-Arg containing peptides linked on the surface to provide non-toxic positive charges for vitreous anchoring. We experimentally confirmed ionic binding as the mechanism of particle trapping in a charge dependent manner, measured particle diffusion rate ex vivo and monitored the half-life in vivo in rat vitreous, and their relations with surface charge of the carriers (*-potential). We further evaluated the adverse effects of fabricated nanoparticles on ocular integrity by histological examination.

Material and Methods

1. Nanoparticle Carrier Design

An illustrated conception of the nanoparticle structure is shown in FIG. 1(a). We chose condensed clusters of cholesteryl dextran (CDEX, 3-5 mole %, hydrophobic domain is presumed roughly at the particle center) as core material of the nanoparticles. Dextran is a biocompatible compound [5] widely used in FDA approved plasma expanders and ocular products. It can form compact spherical nanoparticle carriers with a large variety of molecular weight. We chose the CDEX nanoparticles smaller than the pore size of trabecular meshwork and vitreous collagen fiber meshwork (less than 50 nm).

Cationic peptides providing anchorage were covalently attached to the CDEX particle surface by carbamate attachment through activation of OH groups of sugar units in CDEX. The peptides were designed to contain naturally occurring amino acid sequences from proteins commonly found in plasma or extracellular matrix in order to minimize toxicity and immunogenicity. First, four distinct peptides, containing 4-8 amino acids providing positive charges from 1 to 4 L-Arg groups, were bound covalently to the surface. (As described later, the 4 L-Arg peptide conjugate, with zeta potential of 9-10 mV, was highly immobilized in vitreous humor, and its diffusion was not further studied.) We chose peptides of approximately 50 to 75 A in total length, with 20 to 30 A of cationic groups linked through approximately 30 to 45 A spacers of N-terminal amino-PEG groups (8,12 EG units). The L-Arg groups would be at the distances of 35 to 60 A extended from the particle surface. We estimated 15 to 30 peptides were conjugated to one CDEX particle (Unconjugated particle is 77 kD). This enables Arginine cations to move freely at the particle surface to access and pair with anionic units of HA and similar polymers. Rhodamine B chromophore was also covalently conjugated to the particle surface with a density of about one chromophore per particle as a tag for fluorescence imaging.

The proposed mechanism of the long-lasting nanoparticles in vitreous is shown in FIG. 1(b). Vitreous humor is a transparent gel containing 99% water, with highly cross-linked collagen fiber-hyaluronic acid network to maintain the shape. Hyaluronic acid molecules are anionic and in a random coil structure. HA fills the space between collagen fibers to prevent aggregation. Our nanoparticles are immobilized by the ionic binding between peptides anchored on the particle surface (circles) and hyaluronic acid molecules (strands).

2. Nanoparticle Carrier Synthesis

BOC-amino-PEG(n)-carboxylic acids were obtained from Quanta BioDesign, Plain City, Ohio. Rhodamine (Rh) isocyanate was from Thermo Fisher. Ethanolamine, carbonyldiimidazole (CDI), cholesteryl chloroformate, mono-BOC-ethylenediamine, and dextran (Leuconostoc, 70 kD) were from Sigma Aldrich. Amino-rhodamine (a-Rh) was formed by reaction of Rh-isocyanate with excess mono-BOC-ethylenediamine. It was purified by silica gel chromatography ($CH_2Cl_2$:MeOH, 4:1). BOC was removed with 30% Trifluoroacetic acid (TFA) in $CH_2Cl_2$.

CDEX gel was formed by adding 0.3 g cholesterol chloroformate and one equivalent of triethylamine in 8 mL dichloromethane into 45 mL anhydrous stirred DMSO containing 3.0 g dry Dextran, reacting at 40° C. for 3 hours. After quenching with 45 mL water, the mixture was dialyzed exhaustively against water, and freeze dried. The crude product was re-dissolved in 50 mL water and sonicated (Branson bath) for 2 hours. The solution was then filtered through 0.8 µm, 0.45 µm and 0.2 µm syringe filters consecutively to remove suspended material before final lyophilization In the synthesis of the CDEX, cholesteryl groups covalently attach to 3-5% of the sugar monomers of dextran, in which the attached cholesterol forms a core, thereby condenses the polymer into a compact sphere [6]. Small lipophilic compounds can then be carried in the core while the entire carrier remains water-soluble, presenting a surface of hydrophilic sugars. Those surface hydroxyl groups can be conjugated to multiply hydrophilic drugs or targeting agents such as proteins or peptides. Here we utilize such conjugation to cationic peptides to enhance residence time of nanoparticles in the vitreous humor.

Four peptides for conjugation were synthesized by solid state methods with FMOC coupling methods on RINK amide resin, with final coupling to BOC-PEG-acid, and resin release and de-blocking with TFA. Each Peptide contains an amino-PEG(n)CO- cap at its n-terminus, where n is 8 or 12 ethylene glycol units, as extenders. The structures for peptides containing one to four L-Arg groups (1-Arg, 2-Arg, 3-Arg and 4-Arg) are shown in FIG. 1(a). All were produced and utilized as TFA salts.

CDEX was activated for amino-PEG-peptide coupling by CDI reaction. CDEX (210 mg, 3.0 µmoles) was dried by vacuum evaporation from anhydrous pyridine (2×5 mL), then dissolved in 10 mL anhydrous DMSO. Freshly opened CDI (36 mg; 220 µmoles) in 1 ml DMSO was added dropwise and stirred for 4 hours at 40° C. The CDEX-Im thus formed was dialyzed against water overnight at 4° C. and lyophilized, giving 169 mg product. Nuclear magnetic resonance estimated 58 imidazole groups attached per particle (assuming one 70-kDa dextran molecule forms one CDEX particle).

Peptides were coupled as carbamate to the above CDEX-Im particles as follows: 5 mg of the above CDEX-Im (3.8 µmoles imidazolyl) was dissolved in 0.5 mL water, and pH was then adjusted to 8.0 with $NaHCO_3$. Peptide (3.5 µmoles) dissolved in 0.2 mL of DMF was stirred into the CDEX-Im solution and reacted overnight at 25° C. after which excess Im- was quenched by additional overnight reaction with 4 µl (50 µmoles) of ethanolamine. For each batch, a parallel batch (7 mg CDEX-Im) was reacted overnight with 0.1 mg amino-rhodamine (a-Rh) before quenching with ethanolamine, giving pink colored conjugate. Conjugates were exhaustively dialyzed against water at 4° C., then lyophilized. The product was re-dissolved in water to a concentration of about 0.4 mg/mL and then sterile filtered through 0.2 µm syringe filter.

For fluorescence monitoring a small volume of a-Rh-tagged conjugate was mixed with final concentrated stocks of un-tagged conjugate (1-20 mg/ml) so that their Absorbance at 551 nm was 0.1-0.15. Linkable fluorescence tag was synthesized by modification of Rhodamine isothiocyanate with a 3-fold excess of 2,2'-(ethylenedioxy) bis (ethylamine) and purified by column chromatography on silica gel using a stepwise gradient of methanol in dichloromethane.

3. Characterization of Physical and Chemical Properties

Peptide concentration was estimated by BCA (Pierce) protein assay against a standard curve of free peptide. Zeta potential and size was measured on non-rhodamine product using electrophoretic light scattering and dynamic light scattering, respectively (Zetasizer, Malvern). The Z averaged particle size is 15 nm and the full width at half maximum of the distribution peak is 24 nm. Zeta potentials for 1-Arg, 2-Arg, 3-Arg and 4-Arg peptide conjugates were 0.07 mV, 2.2 mV, 4.6 mV and 9.2 mV respectively (Table 2).

TABLE 2

Physical and chemical properties of nanoparticle carriers.

| Conjugate | Peptides per particle* | Diameter | Zeta potential [unit] |
|---|---|---|---|
| CDEX-1Arg | 19 | 100 nm | 0.07 |
| CDEX-2Arg | 28 | 100 nm | 2.2 |
| CDEX-3Arg | 23 | 100 nm | 4.6 |
| CDEX-4Arg | 19 | 100 nm | 9.2 |

4. Ex Vivo Diffusion Rate Measurements in Rodent Vitreous 4.1. Mathematical Model The rat ocular lens occupies almost two-third of the rat eyeball volume. Rat vitreous body is in a crescent shape and could be roughly considered as a two-dimensional structure [7]. We used a two-dimensional model to calculate the diffusion rate. Assuming right after injection, the drug is uniformly distributed in a circle with a diameter of h, the concentration distribution in cylindrical coordinates is [8]

$$C = \frac{1}{2}C_0\left(\text{erf}\frac{h-x}{2\sqrt{Dt}} + \text{erf}\frac{h+x}{2\sqrt{Dt}}\right), \quad (1)$$

where x is the distance from the origin, t is time, C is the concentration at location x at time t, $C_0$ is the initial concentration, D is the diffusion rate and erf is the error function.

4.2 Preparation of Fresh, Intact Rat Vitreous Gels

Rat (Long-Evans, Charles River) eyeballs were enucleated immediately after euthanasia. We carefully removed conjunctive tissues and placed the eyeballs in a home-made concave holder (6 mm in diameter) with pupil facing up.

Vitreous body is very fragile. Vitreous collagen fibers are tightly linked to both the anterior segment and retina tissues. Vitreous tends to liquefy when removed from the eyeball due to collapse of collagen fibers. To maximally preserve the structure of vitreous, we only removed the cornea and iris for monitoring. We first made a small incision at corneal limbus using a scalpel blade, circumferentially cut along the limbus using a scissor, and separated cornea from sclera. We then carefully picked out iris using a small tweezer. To cancel the dioptric power of the ocular lens, we added a coverslip on top of the opened eyeball. A tiny amount of water was added between coverslip and ocular lens. A ring spacer was used to hold the coverslip from pressing the eye ball.

4.3 Diffusion Rate Measurements

The opened eyeball with the coverslip was placed under a stereo microscope (SMZ1500, Nikon) equipped with a high-sensitive CCD (PixelFly qe, PCO AG, Germany) and a long pass optical filter (FEL0550, Thorlabs; cut-off wavelength: 550 nm) for fluorescence imaging. Two microliter of nanoparticle colloidal gel was injected to the center of vitreous by a microliter syringe (Hamilton, 30 G needle). Nanoparticles carrying four different peptides were separately injected and monitored to determine the influence of various peptide's Zeta potential on the rate of diffusion.

We excited Rhodamine labels using a continuous-wave 532 nm laser (10 mW) and recorded the fluorescence distribution every 5 min. We estimated the fluorescence diffusion area (edge defined as $e^{-1}$ of the center fluorescence intensity) at each time point, and numerically fitted the area to a diffusion equation [8]. For each measurement, the preparation and monitoring was completed within 3 hours. The eyeballs were stored in ice during transportation, and recovered to room temperature before injection and monitoring.

For each measurement, the preparation and monitoring was completed within 3 hours. The eyeballs were stored in ice during transportation, and recovered to room temperature before injection and monitoring.

5. In Vivo Half-Life Measurements 5.1 Intravitreal Injection

Adult rats (250-g Sprague Dawley, Charles River Laboratories) were used for in vivo measurements. Before intravitreal injection, animals were anesthetized by an intraperitoneal injection of a mixture of ketamine and xylazine (ketamine: 11.45 mg/mL; xylazine: 1.7 mg/mL, in saline; 10 mL/kg body weight).

We used a microliter syringe with a 30 G needle (Hamilton) to perform intravitreal injections. The anesthetized rats were placed under a stereomicroscope. We inserted the needle to the posterior chamber from limbus, and held the syringe still. We push the syringe until solution was completely injected to the posterior chamber, and then gently withdrew the needle. Lubricating ophthalmic ointment was applied to eyes after injection.

We intravitreally injected nanoparticle carriers loaded with the cationic peptides of 1-Arg, 2-Arg, 3-Arg and 4-Arg to study the relationship between nanoparticle Zeta potential and its half-life. The injection dose was 1.5 µL, about 2.7% of rat's total vitreous volume [9]. Phosphate-buffered saline of the same volume was injected in the control group.

5.2 Fundus and Fluorescence Imaging

Fundus and fluorescence images were taken every three days in the following week after injection and every 7 days after the first week. Animals were anaesthetized by a mixture of isoflurane and air (2% isoflurane at 3 L/min for 10 minutes and 1.5% at 2 L/min in following experiments). The rat eyes were anesthetized using a drop of 0.5% Tetracaine Hydrochloride ophthalmic solution and dilated using a drop of 1% Tropicamide ophthalmic solution. During imaging, animals were placed on a homemade animal holder. Artificial tears were applied every 2 min to keep the cornea moist.

We took fundus reflectance images to locate the region of interest through retinal landmarks, immediately followed with fluorescence images using a customized high-resolution rodent fundus camera [9]. The reflectance fundus images were taken using a narrow spectral-band illumination (Halogen lamp with band-pass filter; bandwidth: 12.7 nm, center wavelength: 580 nm) to minimize chromatic aberrations. For fluorescence imaging, a 532-nm continues-wave laser was combined into illumination optical path by a 45-degree laser-line mirror. A 550-nm long pass filter (EdmundOptics) was added before the camera to block the excitation light, and let the fluorescence and reflected light to pass. The system's optical resolution was 10 µm. The field of view was 50 degrees. The light powers of reflectance imaging illumination and laser excitation were 0.2 mW and 0.25 mW, respectively, which were below the safety threshold. The exposure times were 0.2 s for fundus imaging and 2 s for fluorescence imaging. All experiments were performed in compliance with the ARVO Statement for the Use of Animals in Ophthalmic and Vision Research and were approved by the Animal Care and Use Committee of Northwestern University.

6. Histological Examination

Rats with no fluorescence detected for two weeks, or 8 months after intravitreal injection (if the fluorescence signal didn't fade away) were euthanized, eyes were enucleated, and immediately fixed in formalin and prepared for histological evaluations. Paraffin sections were stained with hematoxylin/eosin and examined for structural abnormalities and signs of inflammatory infiltrations in masked fashion.

Results

1. Ex Vivo Diffusion Rate In Vitreous

Figure 2:
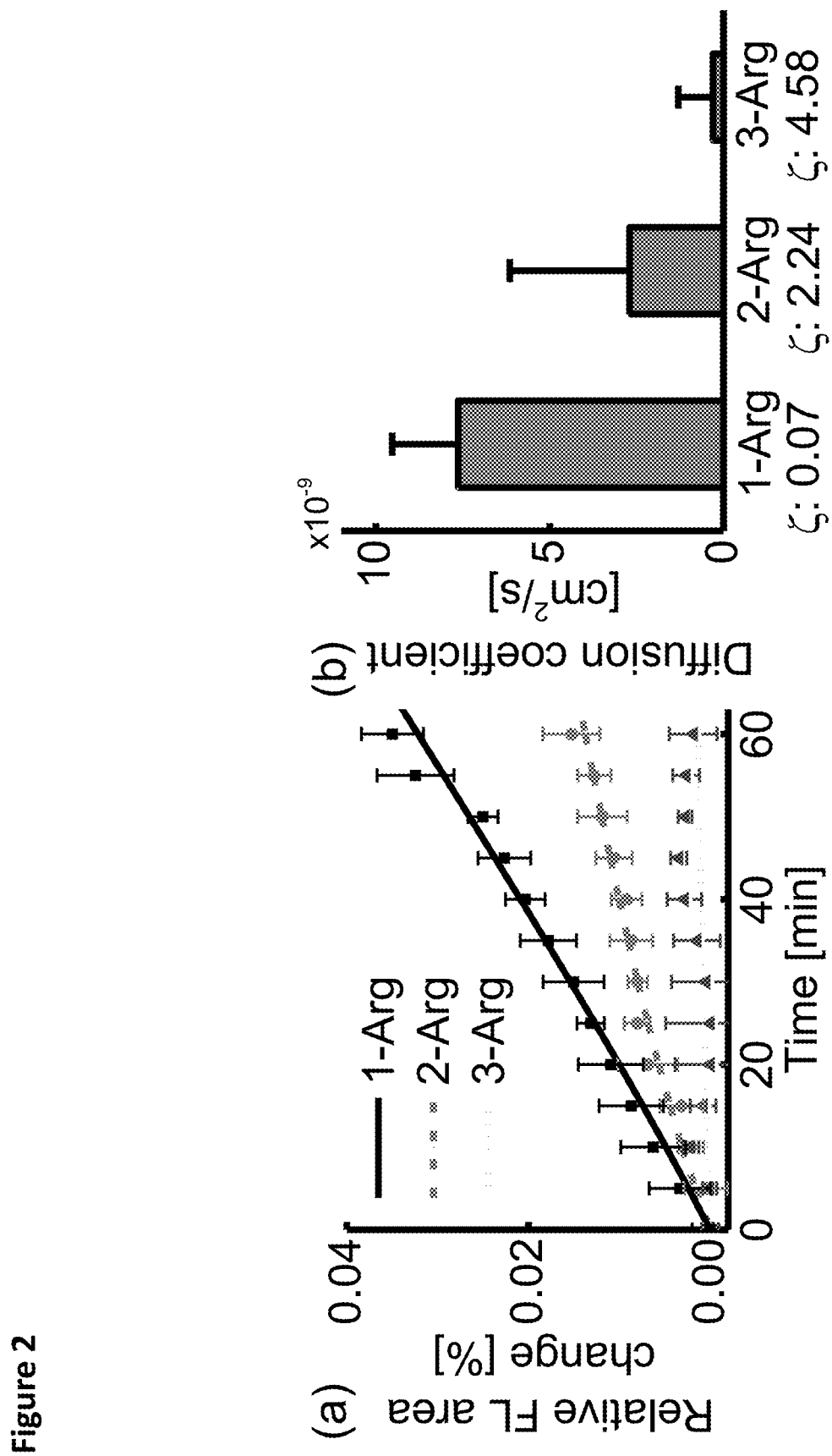
FIG. 2. Ex vivo diffusion coefficient measurements in rat vitreous. (a) Relative fluorescence area change as a function of time. (b) Diffusion coefficient estimated from (a). FL: fluorescence. $\zeta$: Zeta potential, unit mV. The ex vivo nanoparticle diffusion rate of 4-Arg peptide-conjugate (SEQ ID NO.:3) particles are not shown due to the extremely slow particle movement during the observation period. In order to minimize the influence from initial injection conditions, relative area changes were used to calculate diffusion rates. a) Nanoparticle surface modified with peptides containing 1, 2, or 3 L-Arginine groups had distinct diffusion behaviors where nanoparticles modified with 1-Arg peptides (1R) expanded the fluorescent area quickly, 3-Arg peptide (SEQ ID NO:2) modified nanoparticles (3R) only diffused minimally in one hour, and the diffusion of 2-Arg peptide (SEQ ID NO:1) modified nanoparticles (2R) was intermediate. The calculated diffusion coefficients for 1-Arg, 2-Arg, or 3-Arg peptide modified nanoparticles were $7.6\times10^{-9}$ cm$^2$/s, $2.7\times10^{-9}$ cm$^2$/s and $3.0\times10^{-10}$ cm$^2$/s, respectively. b) $\zeta$: Zeta potential, unit mV.

The ex vivo nanoparticle diffusion with time are shown in FIG. 2(a), and the calculated diffusion rates are shown in FIG. 2(b). Diffusion rate of 4-Arg particles ($\zeta$+9.2 mV) are not shown due to the difficulties of measuring the extremely slow particle movement during the observation period. In order to minimize the influence from initial injection conditions, we used relative area changes to calculate diffusion rates. (See supplementary information for more details.)

Nanoparticle surface modified with peptides containing 1, 2, or 3 Arginine groups had distinct diffusion behaviors where nanoparticles modified with 1-Arg peptides ($\zeta$ +0.07 mV) expanded the fluorescent area quickly, 3-Arg peptide modified nanoparticles ($\zeta$ 4.6 mV) only diffused minimally in one hour, and the diffusion of 2-Arg peptide modified nanoparticles ($\zeta$ 2.2 mV) was intermediate. The calculated diffusion coefficients for 1-Arg, 2-Arg, or 3-Arg peptide modified nanoparticles were $7.6 \times 10^{-9}$ cm$^2$/s, $2.7 \times 10^{-9}$ cm$^2$/s and $3.0 \times 10^{-10}$ cm$^2$/s, respectively. The diffusion coefficient of 3-Arg nanoparticles was below the measurement error, since the nanoparticles barely moved in one hour. Longer monitoring time will be needed for more accurate estimation of its diffusion. Compared with the theoretical diffusion coefficient of uncharged particles, the diffusion coefficients of the fabricated nanoparticles was significantly reduced. Ideally, the diffusion coefficient of 50-nm nanoparticles in water is about $1 \times 10^{-7}$ cm$^2$/s. Considering the viscosity of vitreous is three times larger than that of water, the diffusion coefficient of 50-nm nanoparticles in vitreous should be $2.5 \times 10^{-8}$ cm$^2$/s. Compared with this value, 1-Arg modified nanoparticles had a clear effect in reducing the diffusion rate of the carriers by at least 3 fold, while the diffusion coefficient of 2-Arg and 3-Arg nanoparticles were significantly reduced by one and two orders of magnitude. The 2-Arg nanoparticles were comparable to un-modified particles with a diameter of 450 nm, and 3-Arg nanoparticles were comparable to micron-scale particles in terms of diffusion coefficient. The diffusion coefficients were inversely proportional to the Zeta potential of peptide modified nanoparticles, suggesting that the ionic interaction is responsible for reduced particle diffusion.

We confirmed the ionic binding between nanoparticles and hyaluronic acid molecules by competitive binding. We injected the mixture of the nanoparticles and protein molecules with a high Zeta potential (protamine, >20 Arg/35 kD monomer) to the vitreous ex vivo, and monitored the particle diffusion. Protein molecules carrying positive charge can competitively bind to hyaluronic acid. Such competitive binding will increase the nanoparticles' diffusion if nanoparticles are also ionically bound to hyaluronic acid, but will minimally affect the diffusion if the previously observed reduction of nanoparticle diffusion was caused by the trapping of collagen fiber network. In the competition binding assay, we observed significant increases in the nanoparticle diffusion, confirming the ionic biding between the nanoparticles and hyaluronic acid.

2. In Vivo Half-Life Measurement

Figure 3:
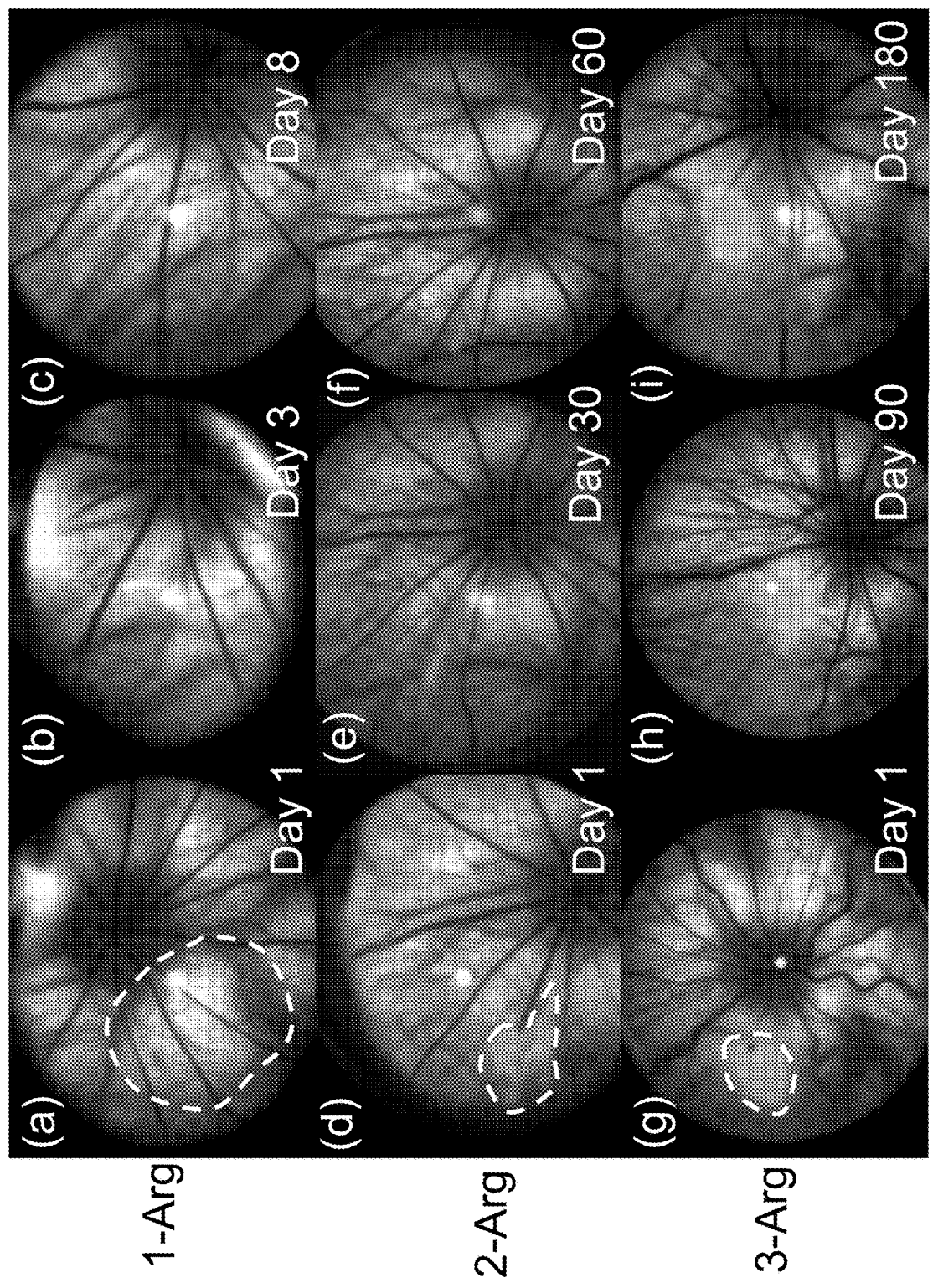
FIG. 3. In vivo observation of nanoparticle carrier in rat eye. Rhodamine fluorescence images were colored in magenta and overlaid with fundus images. Magenta fluorescence images were overlaid with fundus images after a 1 ul injection. the 1-Arg nanoparticles spread into a 6-mm' area in one day after injection, and 90% of fluorescence signal was lost by day 8. The 2-Arg nanoparticles (3d-3f) spread into a 1.7 mm$^2$ area, and the fluorescence was detectable up to two months. 3-Arg nanoparticles (3g-3i) spread to 1.3 mm$^2$, and the fluorescence signal was only slightly reduced after 6 months. The behavior of 4-Arg nanoparticles (not shown) are similar to 3-Arg nanoparticles. By comparing the fluorescence locations determined by retinal vasculature, we found that both 2-Arg and 3-Arg nanoparticles stayed approximately at the original sites of administration.

Examples of the nanoparticle fluorescent maps overlaid with fundus images are shown in FIG. 3. The fluorescence intensities were uniformly normalized by the peak intensity of fluorescence of 3-Arg nanoparticle injection in day one's observation. As shown in FIGS. 3(a) to 3(c), the 1-Arg nanoparticles spread into a 6-mm$^2$ area in one day after injection, and 90% of fluorescence signal diminished by day 8. The 2-Arg nanoparticles (FIG. 3(d)-3(f)) spread into a 1.7 mm$^2$ area, and the fluorescence was detectable up to two months. The 3-Arg nanoparticles (FIG. 3(g)-3(i)) spread to 1.3 mm$^2$, and the fluorescence signal was only slightly reduced after 6 months. The behavior of 4-Arg nanoparticles (not shown) are similar to 3-Arg nanoparticles. By comparing the fluorescence locations determined by retinal vasculature, we found that both 2-Arg and 3-Arg nanoparticles stayed approximately at the original sites, which could be in a practical range for targeting lesions therapeutically. However, the slight changes in location may be attributed to the image angel and eyeball orientation. We estimated the half-life of nanoparticles from the decays of integrated fluorescence intensities. The relative total amount of nanoparticles was estimated by integrating the fluorescence intensity over the image. The distinct fluorescence intensity decay curves of the three type of nanoparticles in the first 60 days are shown in FIG. 3.

Figure 4:
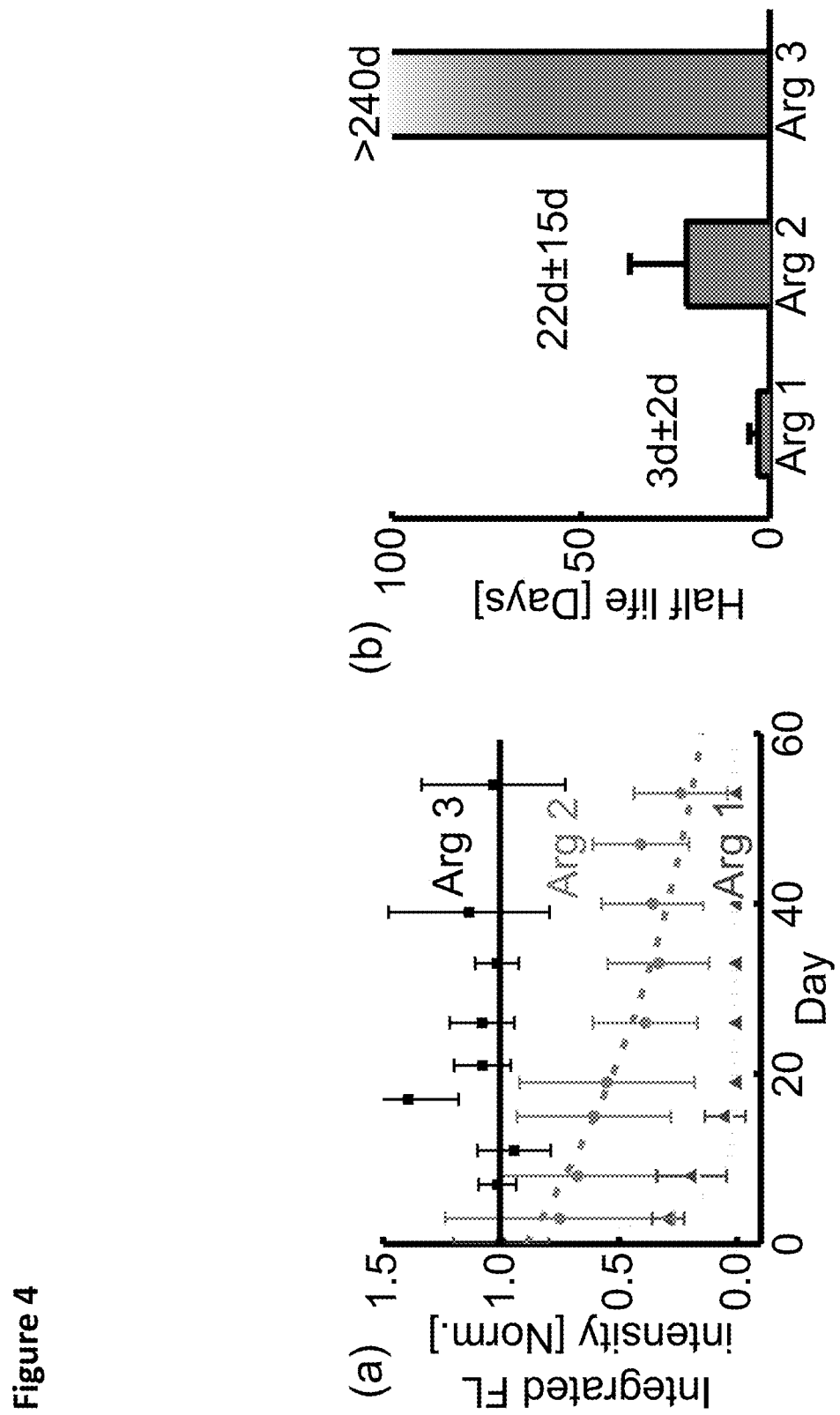
FIG. 4. In vivo half-life estimation of nanoparticle carriers. (a) Integrated fluorescence intensity of 1-Arg (n=6), 2-Arg (n=5) and 3-Arg (n=3) peptide conjugates as functions of time. Solid black line, dash red line and dash dot blue line are the corresponding exponential decay fittings. (b) Half life time of nanoparticle carriers estimated from (a). Error bar represents 95% confidence interval. The half-life for 3-Arg is over 240 days. The monitoring was stopped for terminal histological toxicity exam.

The corresponding half-lives are shown in FIG. 4(b). The half-life of 1-Arg nanoparticles was very short (1 to 5 days), which was comparable to that of some peptides reported in rabbit and human eyes. This may also be due to the small volume of rat vitreous which enables facile escape of weakly charged or uncharged nanoparticles. The 2-Arg nanoparticles had a moderate half-life (7 to 37 days), thus it could extend the interval to the subsequent injection by an additional month. The error bars (confidence intervals) of 1-Arg and 2-Arg nanoparticles were relatively large. This may be attributed to the small sample size and individual physiological differences between each animal. We didn't obtain the half-life of 3-Arg nanoparticles since all animals receiving these nanoparticle injections showed strong fluorescence at the 240th day, a time at which the animals were terminated, thus, suggesting the half-life of 3-Arg nanoparticles in the vitreous is over 240 days.

3. Histological Evaluations

Figure 5:
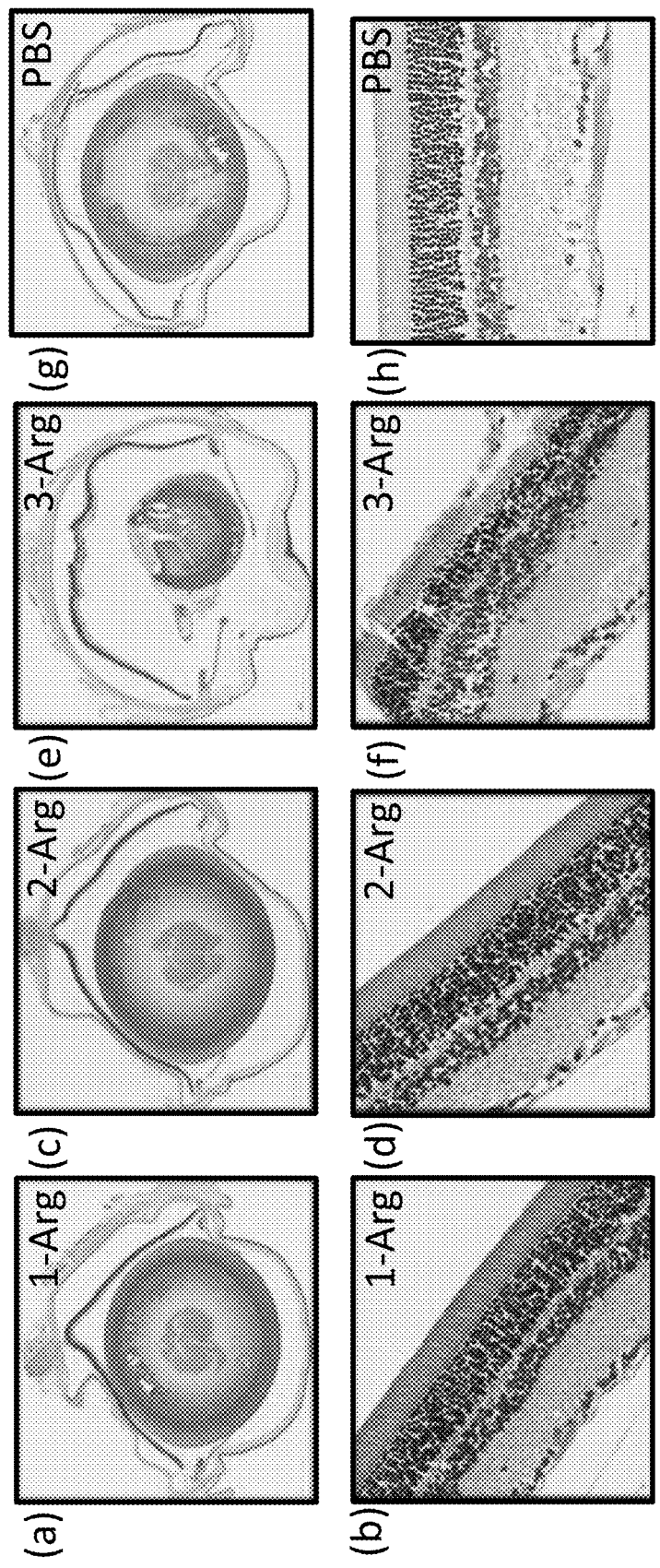
FIG. 5. Representative histological images. (a), (c), (e), and (g) Whole eye sections with injections of 1-Arg, 2-Arg, 3-Arg and PBS (control group), respectively. Scale bar: 1 mm. (b), (d), (f) and (h) the corresponding retinal areas. Scale bar: 50 μm. No tissue or cell damage was observed compared to PBS vehicle control.
Figure 6:
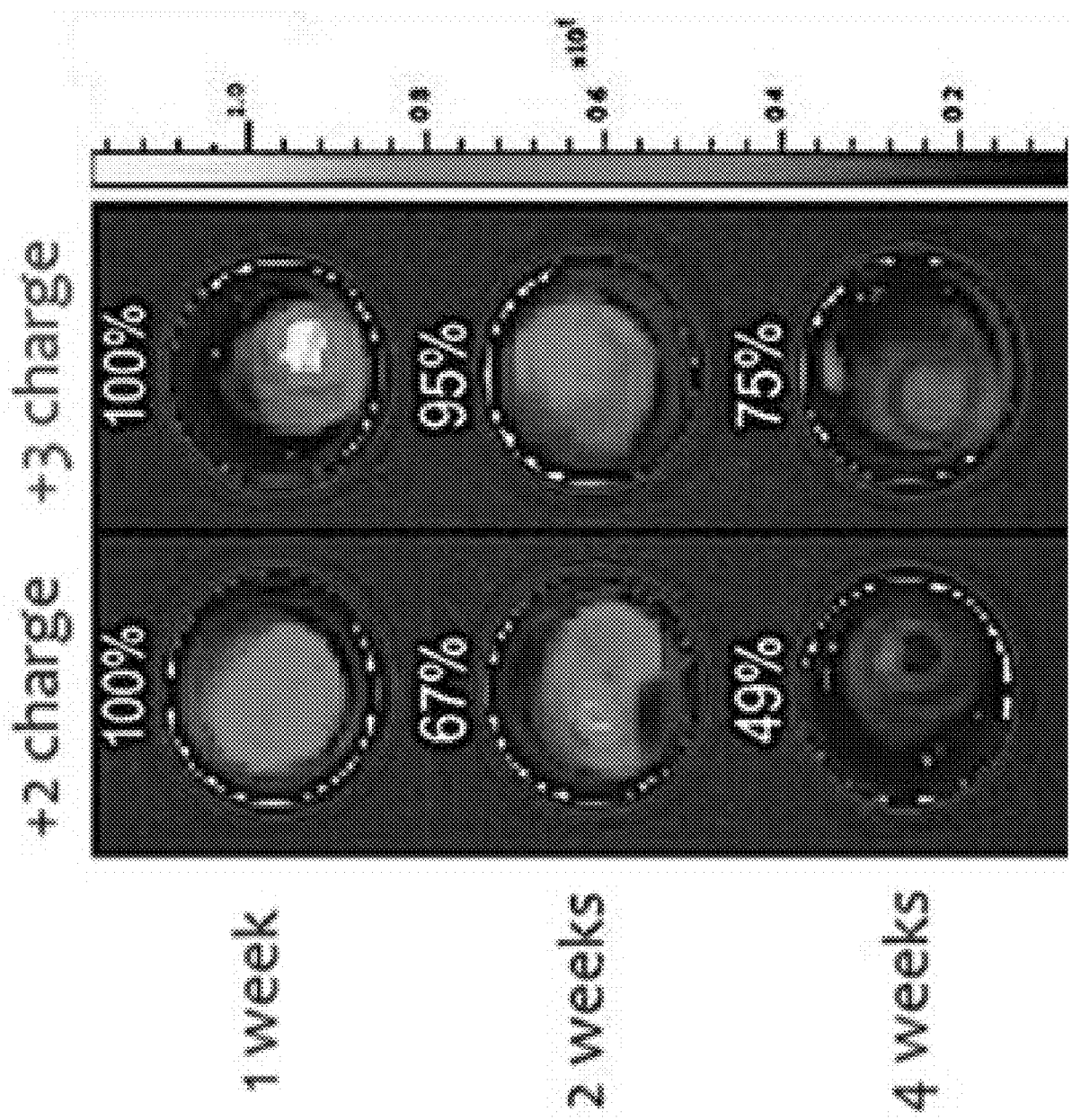
FIG. 6. Peptide conjugates slow diffusion in rabbit vitreous in vivo. 20 ul injections of the same 2-Arg (SEQ ID NO:1) or 3-Arg (SEQ ID NO:2) peptide-conjugated carriers with rhodamine label were injected into eyes of 6 New Zealand rabbits on day 1. Two rabbits were euthanized and had eyes removed and frozen at 1, 2 and 4 weeks. Eyes were cut through while frozen, then thawed cold with liquid facing up. Fluorescence was quantified per eye using an IVIS instrument. Taking 1 week as the zero-time point (100%), ⅓ and 1/20 of the particles were lost after an additional week, and ½ and ¼ of the fluorescent material was lost after two more weeks, when zeta potential=2.2 and 4.6 my respectively.

Following the termination of the experiments, animals receiving various nanoparticles for different durations were sacrificed and their eyes were subjected to histological evaluation. Representative histological images are shown in FIG. 5. We observed no adverse effects on the integrity of ocular structure or infiltration of inflammatory cells.

Discussion

We demonstrated the extended residence of surface modified nanoparticles in vitreous ex vivo and in vivo. We confirmed that such reduced diffusion originated from the ionic binding between cationic peptides and anionic molecules in vitreous, which is consistent with the previous study [10]. One evidence is that the movement of nanoparticles monotonically decreased with increasing Zeta potentials, suggesting the increased binding strength from high surface ionization. The other determine evidence is that in the competitive binding experiment, ionic binding between protamine and hyaluronic acid increased the rate of nanoparticle diffusion. This can be explained by the fact that our nanoparticles anchored themselves to hyaluronic acid by multiply weak ionic interactions. Competitive binding by poly-cationic protamine occupied the hyaluronic acid, causing the increased diffusion of nanoparticles.

The biocompatibility of the polycationic particles is critical to the possible clinical applications. To reduce the total toxicity, we used nano-scale particle carriers and low toxic L-Arg cationic groups for anchoring. The small particle size minimizes inflammatory or obstructive effects. Since particle anchoring no longer relies on entrapment within the vitreous fiber network, the drug carriers are smaller than the mesh of collagen fibers, allowing sub-micron sterile filtration and minimizes residual aggregation on the retina and the likelihood of immune response. Our nanoparticles are smaller than the trabecular drainage meshwork, and should eventually exit from the eye ball with trabecular outflow when detached from vitreous Also, dextran has been used clinically over many years and are safe and readily eliminated [5] via kidney excretion. L-Arg is orders of magnitude safer that most of other cations tested, possibly because cells are able to detoxify L-Arg, through the charge eliminating action of peptide deiminases (PAD), which are known to be present in retina [11]. Peptide arginine, rather than other polymeric forms, may be more amenable to detoxification by PAD. However, PAD presence in vitreous may ultimately convert L-Arg to citrulline on the carrier surface, and limit the residence time. We observed no adverse effects on the integrity of ocular structure or infiltration of inflammatory cells in the histological examination of rat eyes in three types of nanoparticles.

The half-life of the nanoparticles in vitreous is controlled here by adjusting Zeta potential. Zeta potential characterizes the extent of surface ionization, which determines the binding strength and half-life of nanoparticles. There are several ways to control Zeta potential: one is to link peptides with different numbers of positive charged groups. Currently, three discrete Zeta potentials of 0.07, 2.4 and 4.9 result three half-lives of 3 days, 22 days and more than 8 months. To adjust half-life, we could vary the number of peptides on each nanoparticle. We can change the average loading number of 3-Arg peptides or increase 2-Arg peptides to continuously adjust the Zeta potential. By varying the above parameters, we construct versatile drug carriers with a wide range of half-lives to fit multiple intra-ocular delivery objectives for different injection interval requirements.

REFERENCES

[1] National Eye Institute, Prevalence of Adult Vision Impairment and Age-Related Eye Diseases in America, https://nei.nih.gov/eyedata/adultvision_usa, 2016.

[2] K. G. Falavarjani, Q. D. Nguyen, Adverse events and complications associated with intravitreal injection of anti-VEGF agents: a review of literature, Eye, 27 (2013) 787-794.

[3] Q. G. Xu, N.J. Boylan, J. S. Suk, Y. Y. Wang, E. A. Nance, J. C. Yang, P. J. McDonnell, R. A. Cone, E. J. Duh, J. Hanes, Nanoparticle diffusion in, and microrheology of, the bovine vitreous ex vivo, Journal of Controlled Release, 167 (2013) 76-84.

[4] B. J. Zern, H. Chu, A. O. Osunkoya, J. Gao, Y. Wang, A Biocompatible Arginine-Based Polycation, Advanced Functional Materials, 21 (2011) 434-440.

[5] I. Wasiak, A. Kulikowska, M. Janczewska, M. Michalak, I. A. Cymerman, A. Nagalski, P. Kallinger, W. W. Szymanski, T. Ciach, Dextran Nanoparticle Synthesis and Properties, Plos One, 11 (2016).

[6] T. H. Senanayake, G. Warren, S. V. Vinogradov, Novel Anticancer Polymeric Conjugates of Activated Nucleoside Analogues, Bioconjugate Chemistry, 22 (2011) 1983-1993.

[7] A. Chaudhuri, P. E. Hallett, J. A. Parker, Aspheric curvatures, refractive indices and chromatic aberration for the rat eye, Vision Res, 23 (1983) 1351-1363.

[8] J. Crank, The mathematics of diffusion, Oxford university press, 1979.

[9] H. Li, W. Liu, H. F. Zhang, Investigating the influence of chromatic aberration and optical illumination bandwidth on fundus imaging in rats, J. Biomed. Opt., 20 (2015) 106010.

[10] H. Kim, S. B. Robinson, K. G. Csaky, Investigating the movement of intravitreal human serum albumin nanoparticles in the vitreous and retina, Pharmaceutical research, 26 (2009) 329-337.

[11] S. K. Bhattacharya, Retinal Deimination in Aging and Disease, Iubmb Life, 61 (2009) 504-509.

Figure 7:
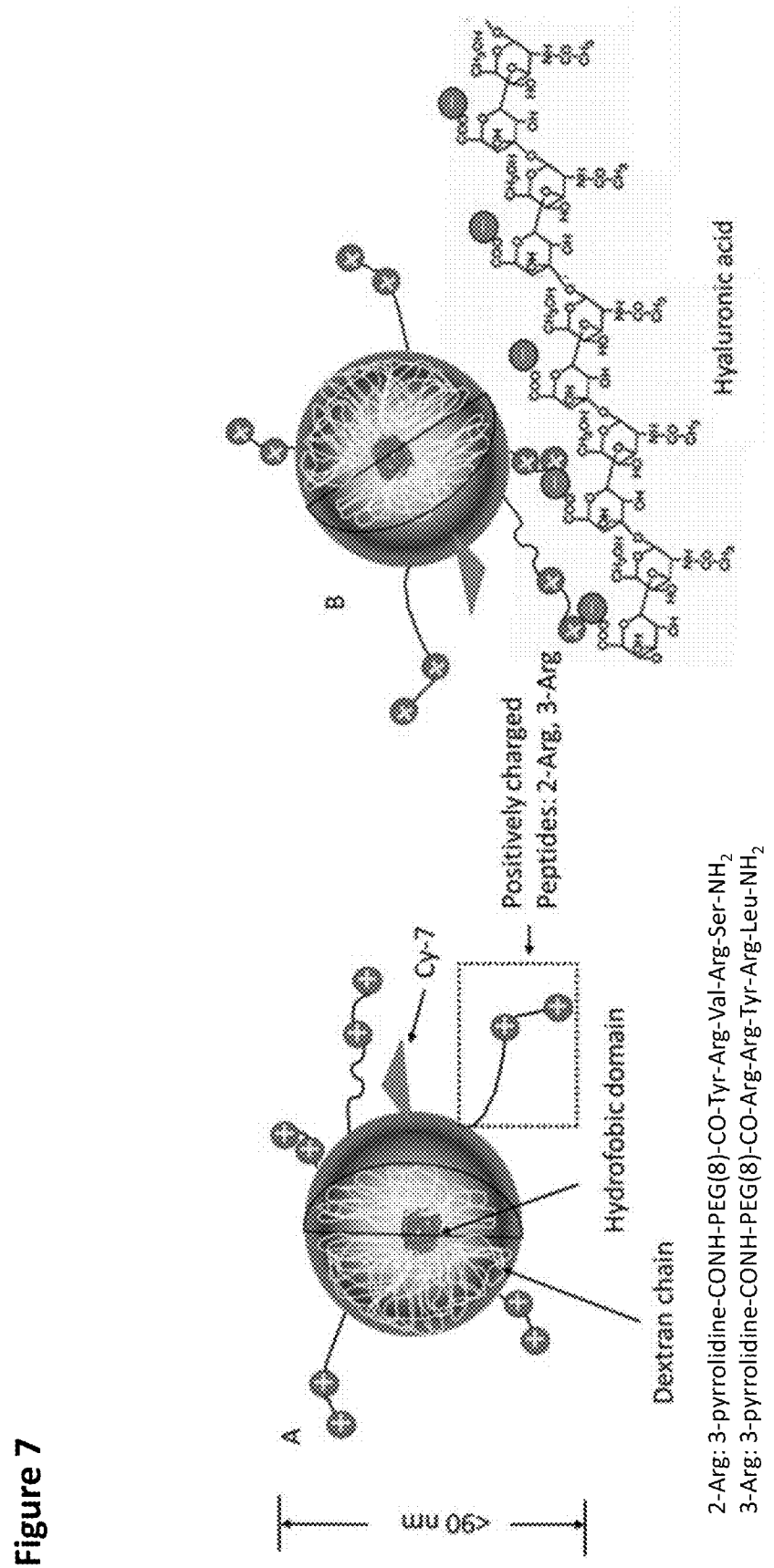
FIG. 7. Schematic of the Cholesterol-dextran nanoparticles tested in-life for rabbit eye clearance. A: Nanoparticle (NP) structure. Hydrophobic domains are at the particle core. B: Particles tagged with <1 mole/NP of Cy7 amine (carbamate-linked) are immobilized in vitreous by ionic binding between peptides on particle surface and hyaluronic acid polymer. Two peptides referred to as either "2-Arg" having two arginine residues and the amino acid sequence 3-pyrrolidine-CONH-PEG(8)-CO-Tyr-Arg-Val-Arg-Ser-NH2 (SEQ ID NO:4), or "3-Arg" having three arginine residues and the amino acid sequence 3-pyrrolidine-CONH-PEG(8)-CO-Arg-Arg-Tyr-Arg-Leu-NH$_2$ (SEQ ID NO:5) were linked to the nanoparticles.

Example 7—Preparation and Testing of Cholesterol-Dextran Nanoparticles with Surface-Linked Peptides in Vitreous Cholesterol-dextran nanoparticles (NP) were labeled with cyanine 7 amine (Cy7) with less than 1 Cy7 per NP. Two types of positively charged peptides were linked on the NP surface, load of 61-64 peptides per particle. (See FIG. 7). As illustrated in FIG. 7, the NP are trapped in vitreous by ionic binding between peptides on the NP surface and hyaluronic acid polymer in the vitreous.

The reaction conditions used for preparing the NP and the physical characteristics of the NP are provided in Table 3.

Figure 10:
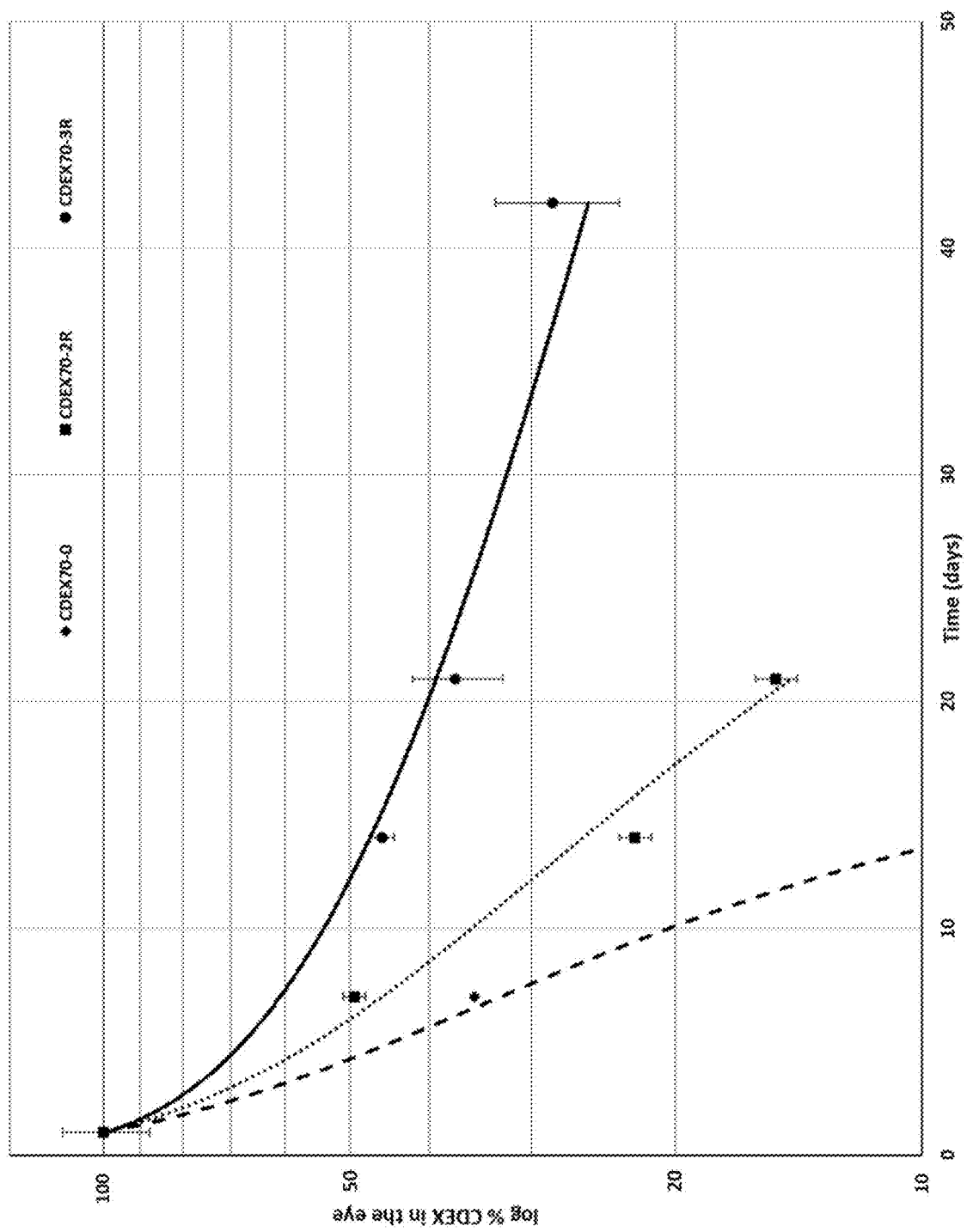
FIG. 10. In vivo charge and zeta potential-dependent loss of NP from rabbit vitreous expressed as a percentage of the first measured photon flux at day 10 post-injection (taken as day 0). Volume of injection: 25$_1$1.1; nanocarrier concentration: 3 mg/ml. [Control: CDEX70-0: (n=2). CDEX70-2R; 64 peptides per particle by BCA (n=3) and CDEX70-3R; 61 peptides per particle by BCA (n=3)]. Half-lives: CDEX-0: 4 days; CDEX-2R: 7 days; CDEX70-3R: 13 days. 2R and 3R peptides are respectively (SEQ ID NO:4) and (SEQ ID NO:5) linked as carbamates of 3pyrrolidineCO-amido-PEG8-CO-peptide to Cy7-CDEX70. Cy7 amine is carbamate-linked at <1 mole/mole NP.
Figure 11:
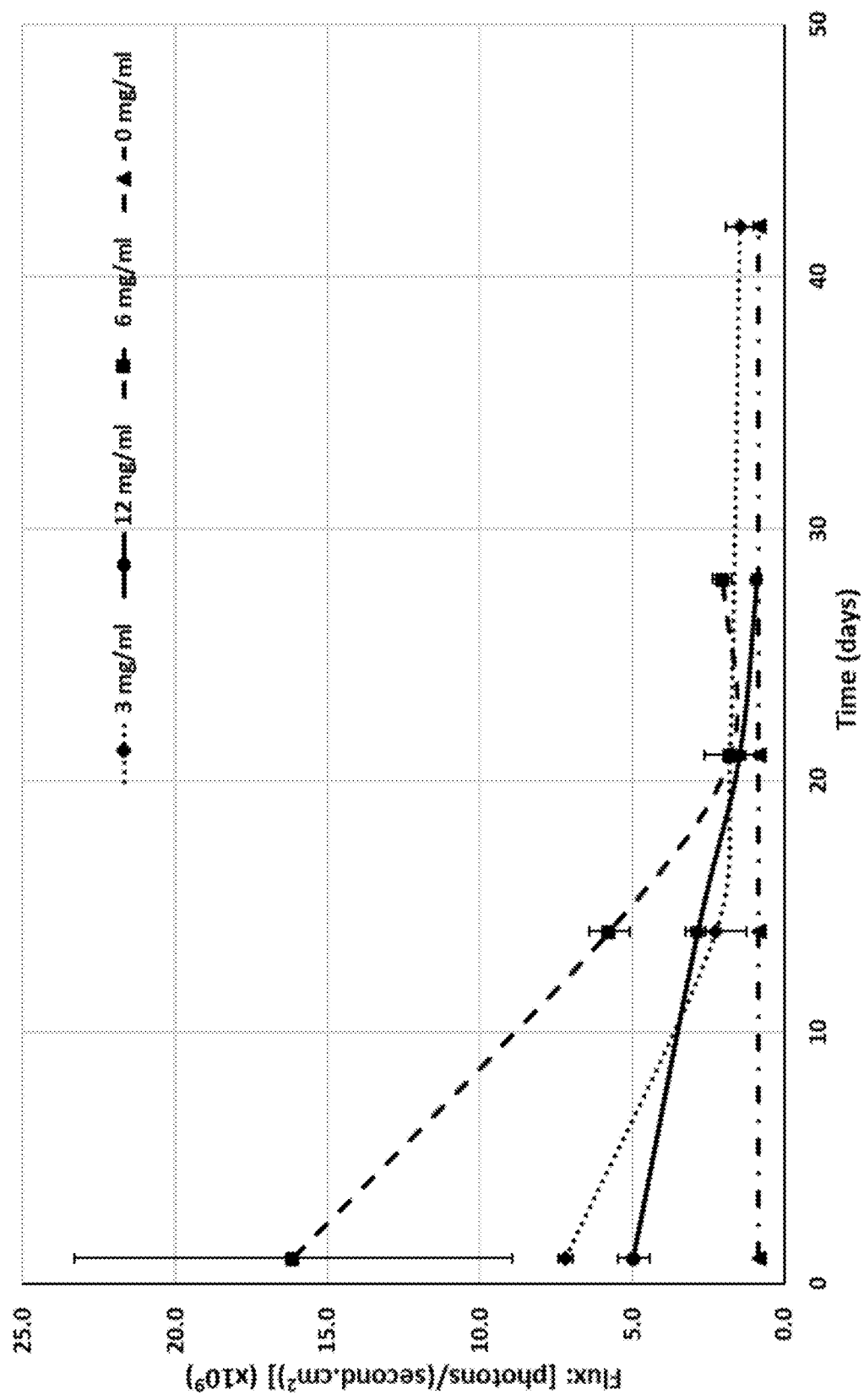
FIG. 11. Initial dose dependence of in vivo loss of NP from rabbit vitreous expressed as percentage fluorescent photon flux compared to the first measurement at day 10 post-injection of 20 ul (taken as day 0) of CDEX70-2R64-Cy7 at 4 different concentrations [Control: 0 mg/ml (n=6). 3 mg/ml (n=3). 6 mg/ml (n=2) and 12 mg/ml (n=2)]. This indicates consistent slowing of nanoparticle loss up to 120 μg injected 2R conjugates, but large initial loss, implying binding capacity is exceeded at 240 μg in 2 ml rabbit eye.
Figure 12A:
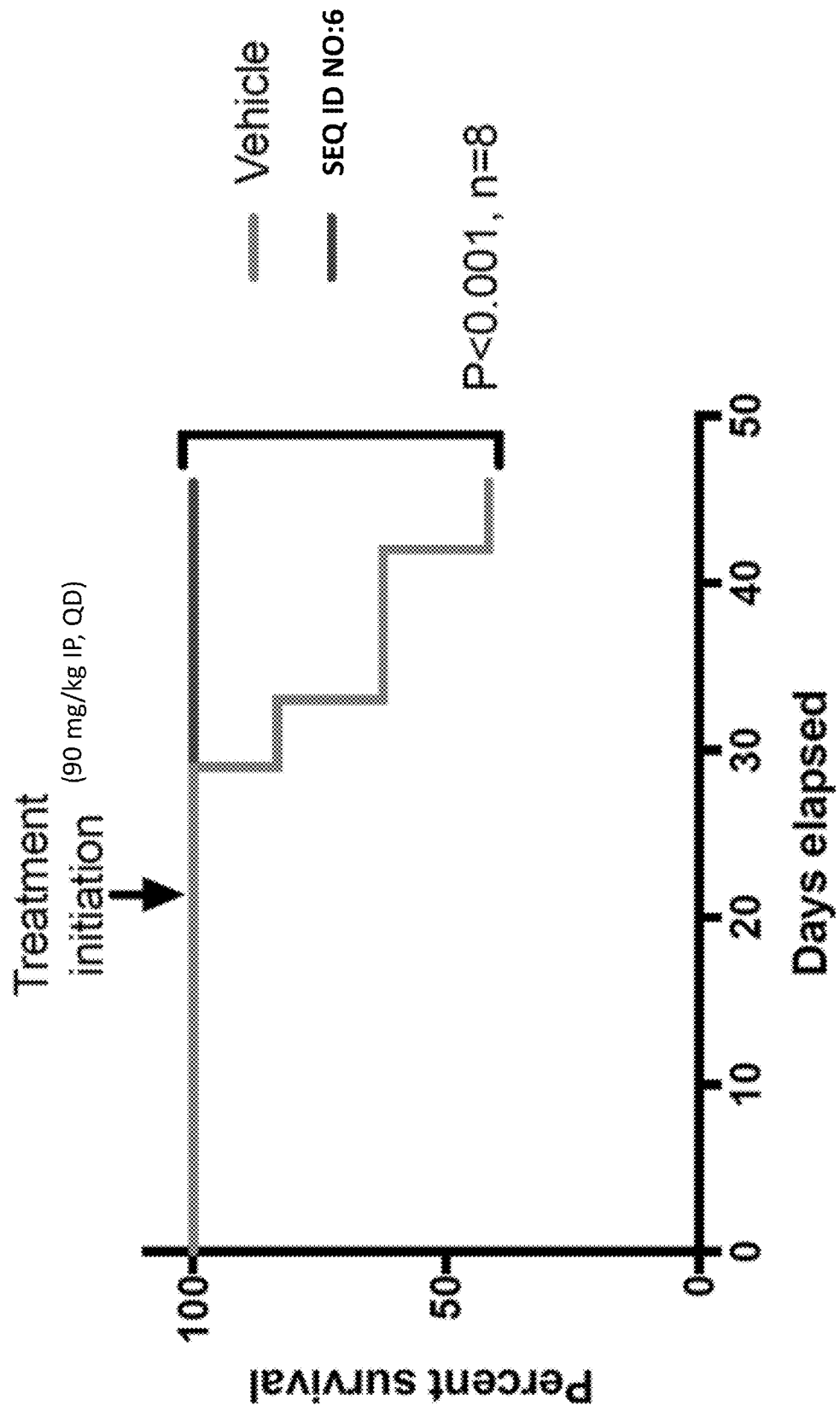
FIG. 12A. Survival curve for mice bearing peritoneal ID8 mouse ovarian tumor administered IP, QD of bioactive 2R anti-tumor nonapeptide, vs. vehicle starting day 22 after tumor inoculation (adipic-Sar-Tyr-Asn-Leu-Tyr-Arg-Val-Arg-Ser-NH$_2$) (SEQ ID NO:6).
Figure 12B:
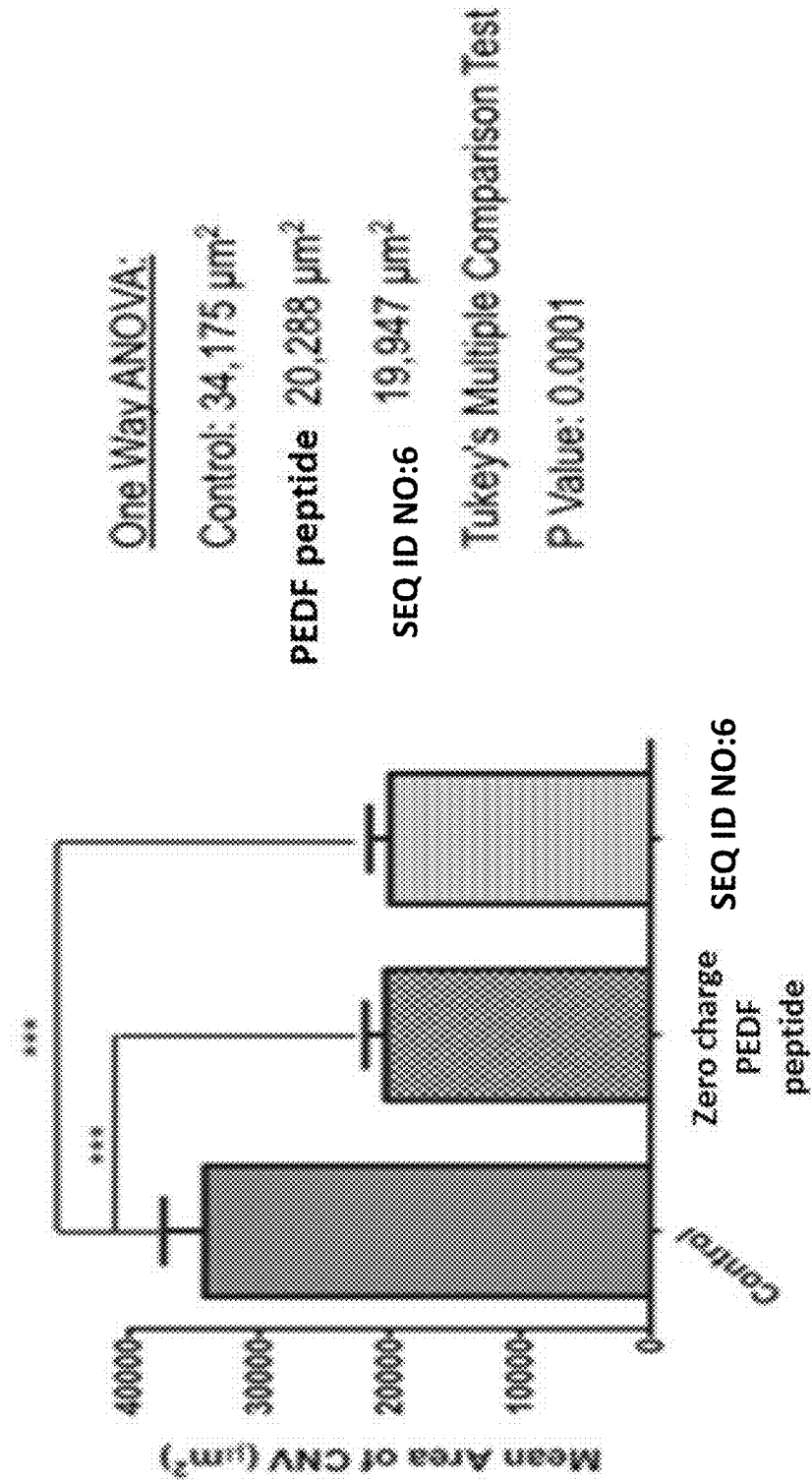
FIG. 12B. Retinal protective activity of the same peptide is seen in reduction of laser-induced choroidal neovascularization (CNV), a model of neovascular macular degeneration. A single injection of 1-ul 4 mg/ml peptide (SEQ ID NO:6) or control is injected into mouse vitreous 2 days before laser wounding of the retina. Angiogenesis markers are detected by antibody stain, 14 days later.
Figure 13:
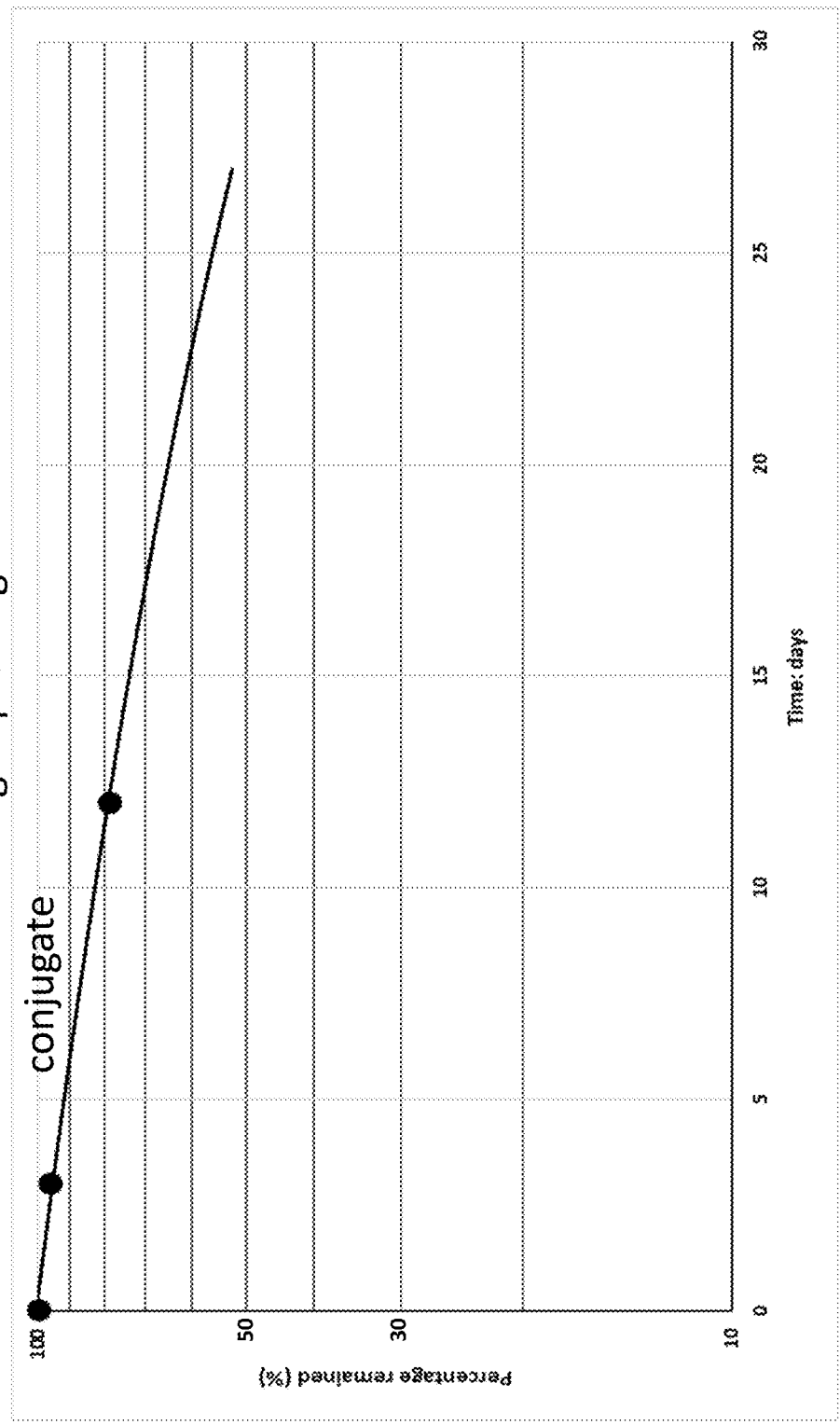
FIG. 13. Bioactive SEQ ID NO:6 (FIG. 12A, B) is linkable to CDEX as 3-pyrrolidinol ester prodrug. The bridged prodrug linking form of bioactive peptide (SEQ ID NO:6) and its attachment to CDEX is detailed herein. 44 mg/ml conjugate containing 76 uM linked peptide was incubated in HEPES buffer, pH7.4 at 37° C. At 0, 3 and 7 day time points filterable peptide (10 kD MWCO) centrifugal filter was identified as SEQ ID NO:6 by HPLC and quantified by UV spectrum of the filtrate, where 100 uM peptide has peak OD=0.22 at 276 nM. A semi-log loss curve shows half-life of 28 days, releasing bioactive peptide at approximately 2% per day of the NP-bound amount.

Retention of the NP in vitreous was tested in vivo in rabbits. 25 µl of CDEX70-2R-Cy7 (SEQ ID NO:4) 3 mg/ml or CDEX70-3R-Cy7 (SEQ ID NO:5) 3 mg/ml was administered by intravitreal injection and imaged via an IVIS scan after 4 weeks and nine weeks. Left: 4-week experiment. (See FIG. 9). The in vivo diffusion dependent loss of NP from rabbit vitreous expressed as percentage of the first measurement at day 10 post-injection (taken as day 0) is provided in FIG. 10. The determined half-lives of the NP is as follows: CDEX-0-Cy7: 4 days; CDEX-2R-Cy7: 7 days; CDEX70-3R-Cy7: 13 days. In vivo diffusion-dependent loss of NP from rabbit vitreous expressed as Flux of the first measurement at day 10 post-injection (taken as day 0) of CDEX70-2R-Cy7 at 4 different concentrations [Control: 0 mg/ml (n=6). 3 mg/ml (n=3). 6 mg/ml (n=2) and 12 mg/ml (n=2)] is provided in FIG. 11. The sample at 12 mg/ml was observed to be eliminated faster than other concentrations which might be because the retention capacity of hyaluronic acid was exceeded.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

TABLE 3

Reaction Condition and Physical Characteristics of the Nanoparticles (NP).

A

| NP | pNP excess per CDEX | pNP/CDEX | Pept excess per CDEX | Cy7 excess per CDEX |
|---|---|---|---|---|
| CDEX-Cy7 | 1,400 | 70 | 0 | 5 |
| CDEX-2R-Cy7 | 1,400 | 167 | 200 | 5 |
| CDEX-3R-Cy7 | 1,400 | 144 | 200 | 5 |

B

| NP | Yield (%$_{w/w}$) | Particle size (nm) | ζ (mV) | Pept/CDEX | Possitive charge/CDEX | Cy7/CDEX |
|---|---|---|---|---|---|---|
| CDEX-0-Cy7 | 51.42 | 152.27 ± 2.20 | −0.61 ± 0.08 | 0 (0) | 0 (0) | 0.16 |
| CDEX-2R-Cy7 | 81.29 | 85.21 ± 14.98 | 3.88 ± 1.15 | 62 (64) | 124 (128) | 0.24 |
| CDEX-3R-Cy7 | 91.30 | 81.69 ± 7.44 | 6.34 ± 1.28 | 67 (61) | 201 (183) | 0.28 |

A: Conditions for the activation of CDEX with 4-nitrophenyl chloroformate (pNP) and conjugation of peptides (Pept) and dye (Cy7) to the nanocarrier.
B: Characterization and measurement of the NP by dynamic light scattering and electrophoretic mobility (n = 3). Number of peptides per particle of CDEX; the quantification of peptide was determine by absorbance of tyrosine ($EC_{Tyr}$ = 1,100 $M^{-1}cm^{-1}$) and BCA (result in brackets and bold). Number of molecules of Cy7; the quantification of cyanine 7 was determine also by absorbance ($EC_{Cy7}$ = 199,000 $M^{-1}cm^{-1}$).

The UV-VIS spectrum for CDEX-peptide-Cy7 nanoparticles, which contain a tyrosine residue, and for CDEX peptide-Cy7 exhibits an absorption peak at about 275 nm (peptide tyrosine) and also exhibit an absorption peak at >700 nm. The fluorescence emission signal observed in the in vivo rabbit experiment described below corresponds to the long wavelength absorption peak of Cy7, excited at 745 nm in the IVIS instrument.

We claim:

1. Nanocarriers that are biodegradable or that can be excreted and have a net positive surface charge and zeta potential between about +2 to about +20 mV, wherein the net positive surface charge is provided by peptides that are covalently attached to the surface of the nanocarriers via carbamate conjugation between hydroxyl groups on the surface of the nanocarriers and an amino group appended to the peptide N-terminus, wherein the amino acid sequence of the covalently attached peptides includes at least 2 L-Arginine residues, no more than 4 L-Arginine residues, and no other charged amino acids other than L-Arginine residues.

2. The nanocarriers of claim 1, wherein the nanocarriers comprise a polymeric carbohydrate and are transparent, and preferably have a diameter that permits for filter sterilizing.

3. The nanocarriers of claim 1, wherein the nanocarriers comprise dextran which optionally is a condensed dextran hydrogel, chitosan, pullulan, or a dendrimer.

4. The nanocarriers of claim 1, wherein the peptides comprise C-terminal amide groups.

5. The nanocarriers of claim 1, wherein the peptides comprise at least 2 amino acids and no more than 11 amino acids.

6. The nanocarriers of claim 1, wherein the amino acid sequence of the attached peptides comprises an amino acid sequence of a human protein that is secreted into the extracellular matrix or that is found in vitreous humor, blood, urine, or saliva, or has an amino acid sequence that is at least 75% identical with the corresponding sequence from the human protein that is secreted into the extracellular matrix or that is found in vitreous humor, blood, urine, or saliva.

7. The nanocarriers of claim 1, wherein the peptides include at their N-terminus a neutral amino acid residue selected from the group consisting of sarcosine, or beta-alanine.

8. The nanocarriers of claim 1, wherein the peptides are covalently attached to the nanocarriers via conjugation between hydroxyl groups on the surface of the nanocarriers and free amino groups N-terminally linked to the peptides.

9. The nanocarriers of claim 1, wherein the amino group is selected from the group consisting of a free alpha amino group on the peptides, a free beta, gamma, delta or epsilon amino acyl group on the peptides.

10. The nanocarriers of claim 1, wherein the peptides are covalently attached to the surface of the nanocarriers via amide conjugation between carboxyl groups on the surface of the nanocarriers and an amino group appended to the peptide N-terminus, wherein the amino group is selected from the group consisting of a free alpha amino group on the peptides, a free beta, gamma, delta or epsilon amino acyl group on the peptides.

11. The nanocarriers of claim 1, wherein the peptides have a formula: B-Z-AA0-(AA1)$_n$-Y, where n is an integer between 1 and 10 where no less than two AA and no more than 4 AA are L-arginine, and all other AA are neutral, wherein:

B is present or absent, and when B is present, B is selected from the group consisting of amino-n-butoxy, amino-ethoxyethyloxy, amino-piperidyl (3, or 4)-oxy, amino-pyrrolidinyl (3)-oxy, amino-benzyl (3, or 4)-oxy, aminoethylamido-valeric acid (4)-oxy, amino-cyclohexyl (3, or 4)-oxy, and amino-cyclopentyl (3)-oxy;

Z is absent or present, and when Z is present, Z is a dicarboxylic acid, including suberic, adipic, glutaric, dimethylglutaric, succinic in half amide bond to AA0 or AA1, where the OH group of an above amino alcohol, B is bonded as an ester to the free dicarboxylic acid group in half-amide linkage to or AA1;

AA0 is present or absent, and when present, AA0 is selected from the group consisting of L-arginine, a naturally occurring amino acid with an uncharged side chain, beta-alanine, and L-proline;

AA1 is L-arginine or a naturally occurring amino acid with an uncharged side chain;

Y is an amide, a mono-substituted or di-substituted alkyl amide, or a PEG (4-12) amide;

with the proviso that:
the peptides have a net positive charge and their multiple linkage to carrier produces nanoparticles having zeta potential between about +2 to about +20 mV; when peptide comprises from about 10% to about 50% of the conjugate mass, whereby ester hydrolysis slowly reduces peptide content and zeta potential of the nanoparticle, leading to accelerating vitreal loss.

12. The nanocarrier of claim 11 in which the appended esterified dicarboxypeptide [Z-AA0-$(AA1)_n$-Y], comprising from about 10% to about 50% of the total nanocarrier mass, is bio-active, as in anti-angiogenic peptide adipic-Sar-Tyr-Asn-Leu-Tyr-Arg-Val-Arg-Ser-amide (SEQ ID NO:6), thus acting simultaneously as a prodrug as well as an anchor to slow diffusion.

13. The nanocarriers of claim 11, wherein B is an amino-PEG-carboxylic acid having between 4 and 12 ethylene glycol units in amide bond to AA0 or AA1, and Z is absent.

14. The nanocarriers of claim 1 in which amino-PEG-OH or amino-PEG-OMe of molecular weight ranging from 200 to 2,000 grams/mole are additionally appended to carriers through carbamate or amide bonds while comprising from about 10% to about 50% of the conjugate mass.

15. The nanocarriers of claim 1, wherein the peptides are selected from the group consisting of:

$NH_2$-PEG(8-12)-CO-Gly-Val-Ile-Thr-Arg-Ile-Arg-$NH_2$ (SEQ ID NO:1);

$NH_2$-PEG(8-12)-CO-Arg-Arg-Ser-Ser-Arg-Arg-Trp-$NH_2$ (SEQ ID NO:3);

$NH_2$-PEG(8-12)-CO-Tyr-Arg-Val-Arg-$NH_2$ (SEQ ID NO:4);

NH$_2$-PEG(8-12)-CO-Arg-Arg-Tyr-Arg-Leu-NH$_2$ (SEQ ID NO:5);

NH$_2$-PEG(8-12)-CO-Arg-Arg-Ser-Ser-Arg-Arg-NH$_2$ (SEQ ID NO:9);

and the N-terminal amino group is in covalently linked to a hydroxyl on the surface of the particles through an amide linkage or carbamate linkage.

16. The nanocarriers of claim 1, wherein the peptides are selected from the group consisting of:

3-pyrrolidine-CONH-PEG(8)-CO-Tyr-Arg-Val-Arg-Ser-NH$_2$ (SEQ ID NO:4); and 3-pyrrolidine-CONH-PEG(8)-CO-Arg-Arg-Tyr-Arg-Leu-NH$_2$ (SEQ ID NO:5).

17. The nanocarriers of claim 11, wherein the appended esterified dicarboxypeptide [B-Z-AA0-(AA1)$_n$-Y] comprising from about 10% to about 50% of the total nanocarriers mass is pyrrolidinyl (3)-oxy-adipic-Sar-Tyr-Asn-Leu-Tyr-Arg-Val-Arg-Ser-amide (SEQ ID NO:6).

18. A pharmaceutical composition comprising the nanocarriers of claim 1 and a suitable pharmaceutical carrier.

19. A method comprising administering the pharmaceutical composition of claim 18 to a subject in need thereof.

\* \* \* \* \*